United States Patent
Lam et al.

(10) Patent No.: US 6,221,676 B1
(45) Date of Patent: Apr. 24, 2001

(54) DNA ENCODING HUMAN LEUKOTRIENE $C_4$ SYNTHASE, POLYPEPTIDES AND USES THEREFOR

(75) Inventors: Bing K. Lam, Roslindale; John F. Penrose, Norwood; K. Frank Austen, Wellesley, all of MA (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 08/986,837

(22) Filed: Dec. 8, 1997

Related U.S. Application Data

(62) Division of application No. 08/246,991, filed on May 20, 1994.

(51) Int. Cl.$^7$ .................................................. G01N 33/543
(52) U.S. Cl. .................. 436/518; 424/130.1; 424/139.1; 424/141.1; 424/146.1; 424/152.1; 424/158.1; 435/7.4; 435/193; 536/23.2; 536/23.5
(58) Field of Search ............................... 424/130.1, 139.1, 424/141.1, 146.1, 152.1, 158.1; 435/704, 193; 536/23.2, 23.5; 436/518

(56) References Cited

PUBLICATIONS

Lewis et al, "leukotrienes and other products of the 5–lipoxygenase pathway", N.Eng. J. Med., vol. 323, No. 10, pp. 645–655, Jan. 1, 1990.*

Campbell, "General properties and applications of monoclonal antibodies", in, Monoclonal Antibody Technology. Elsevier Science Publishers B.V., The Netherlands, pp. 1–3 and 29, Jan. 1, 1984.*

Maurer et al, "Proteins and polypeptides as antigens", Methods in Enzymology, vol. 70, pp. 49–70, Jan. 1, 1980.*

Tanihiro Yoshimoto et al., "Properties of Highly Purified Leukotriene $C_4$ Synthase of Guinea Pig Lung", J. Clin. Invest., vol. 81, p. 866–871, Mar. 1988.

Tanihiro Yoshimoto et al., "Isolation and Characterization of Leukotriene $C_4$ Synthetase of Rat Basophilic Leukemia Cells", Proc. Natl. Acad. Sci., vol. 82, p. 8399–8403, Dec. 1985.

John F. Penrose et al., "Purification of Human Leukotriene $C_4$ Synthase", Proc. Natl. Sci., vol. 89, p. 11603–11606, Dec. 1992.

Mats Söderström et al., "Leukotriene C Synthase in Mouse Mastocytoma Cells", Biochem. J., vol. 250, p. 713–718, 1988.

Michael K. Bach et al., "Solubilization and Characterization of the Leukotriene $C_4$ Synthetase of Rat Basophil Leukemia Cells: A Novel, Particulate Glutathione S–Transferase", Archives of Biochemistry and Biophysics, vol. 230, No. 2, p. 455–465, May 1, 1984.

Takashi Izumi et al., "Solubilization and Partial Purification of Leukotriene $C_4$ Synthase From Guinea–Pig Lung: A Microsomal Enzyme With High Specificity Towards 5,6–epoxide leukotriene $A_4$", Biochimica et Biophysica Acta, vol. 959, p. 305–315, 1988.

Donald W. Nicholson et al., "Purification of Human Leukotriene $C_4$ Synthase From Dimethylsulfoxide–Differentiated U937 Cells", Eur. J. Biochem., vol. 209, p. 725–734, 1992.

Donald W. Nicholson et al., "Purification of Homogeneity and the N–Terminal Sequence of Human Leukotriene $C_4$ Synthase: A Homodimeric Glutathione S–Transferase Composed of 18–kDa Subunits", Proc. Natl. Sci., vol. 90, p. 2015–2019, Mar. 1993.

* cited by examiner

*Primary Examiner*—Rodney P. Swartz
(74) *Attorney, Agent, or Firm*—Choate, Hall & Stewart; Brenda Herschbach Jarrell; Stanley C. Mah

(57) ABSTRACT

An isolated nucleotide sequence encoding human leukotriene $C_4$ synthase or variants of human leukotriene $C_4$ synthase polypeptide, is provided. One embodiment is an isolated DNA sequence (SEQ ID NO.:1) encoding a human leukotriene $C_4$ synthase polypeptide, that has three hydrophobic transmembrane domains. Also described are recombinant cells and plasmids containing the foregoing isolated DNA, preferably linked to a promoter. Isolated leukotriene $C_4$ synthase is provided, having at least three hydrophobic transmembrane domains (SEQ ID NO.:2). Portions of the foregoing isolated human leukotriene $C_4$ synthase polypeptide are also described. Antibodies with selective binding specificity for the polypeptides of the invention also are provided as well as a sensitive method for assay of human leukotriene $C_4$. Methods for producing leukotriene C4 synthase as well as methods for testing for modulators of leukotriene C4 synthase activity are also described.

10 Claims, 3 Drawing Sheets

FIG. 1B

FROM FIG. 1A

```
TTC GCG CGC CTC CGC TAC TTC CAG GGC TAC GCG GCG TCC GCG CAG    360
CTC AGG CTG GCA CCG CTG TAC GCG AGC GCG CGC GCC CTC TGG CTG    405
CTG GTG GCG CTG GCT GCG CTC GGC CTG CTC GCC CAC TTC CTC CCG    450
GCC GCG CTG CGC GCC GCG CTC CTC GGA CGG CTC CGG ACG CTG CTG    495
CCG TGG GCC TGA GACCAAGGCCCCCGGGCCGACGGAGCCGGGAAAGAAGAGCCGG    550
AGCCTCCAGCTGCCCGGGGAGGGGCGCTCGCTTCCGCATCCTAGTCTCTATCATTAAA    609
GTTCTAGTGACCCG(polyA)    622
```

DNA ENCODING HUMAN LEUKOTRIENE C$_4$ SYNTHASE, POLYPEPTIDES AND USES THEREFOR

This is a divisional of copending application Ser. No. 08/246,991 filed on May 20, 1994.

This invention was made with U.S. Government support under NIH Grant HL 36110, AI22531, AR36308 and RR 05950. The U.S. Government has certain rights to this invention.

BACKGROUND OF THE INVENTION

Leukotrienes are lipid-derived cell mediators that are released in response to a variety of immunologic and inflammatory stimuli. They are products of arachidonic acid metabolism derived through the 5-lipoxygenase pathway. Briefly, the initial step in leukotriene production involves oxygenation of arachidonic acid to produce 5S-hydroperoxy-6,8-trans-11,14 cis-eicosatetraenoic acid (5-HPETE), a subsequent dehydrase step producing the epoxide intermediate, 5,6-trans-oxido-7,9-trans-11,14-cis-eicosatetraenoic acid (LTA$_4$). Two routes of metabolism from LTA$_4$ lead to the production of biologically active products. One of these pathways involves conjugation of LTA$_4$ with glutathione (GSH) via LTC$_4$ synthase to produce the sulfur-containing leukotriene 5S-hydroxy-6R-S-glutathionyl-7,9-trans-11,14 cis-eicosatetraenoic acid (LTC$_4$). It is generally believed that LTC$_4$ synthase is a member of the glutathione-S transferase enzyme family.

LTC$_4$ has been implicated in a wide variety of diseases and pathologic conditions. LTC$_4$ has been identified in fluids from psoriatic lesions and bronchial secretions associated with adult respiratory distress syndrome and neonatal pulmonary hypertension. For review, see Lewis et al., New England J. Med., 323: 645 (1990), incorporated herein by reference.

Although the other enzymatic members of the 5-lipoxygenase pathway have been cloned, the cloning of LTC$_4$ synthase has been problematic. This is partly because the synthase is very labile in partially purified form and because the endogenous production of LTC$_4$ synthase in normal human cells is extremely small. LTC$_4$ synthase is present only in limited types of normal human cells, namely granulocytes derived from bone marrow. Moreover, oligonucleotides developed from the N-terminal region of the LTC$_4$ synthase polypeptide have not been specific enough to develop an effective screen because the N-terminal region is highly degenerate. In addition, an effective immunoassay for LTC$_4$ which relies on incubation of substrate has also been problematic since breakdown products of the substrate have been shown to cross-react with antibodies used in the assay.

It has already been established that inhibitors of 5-lipoxygenase and of the cell receptors for leukotrienes are of substantial efficacy in the management of patients with bronchial asthma. Given that that are only three points at which the leukotriene metabolic system can be disrupted: the activation and function of 5-lipoxygenase; the receptor for the leukotriene; or the function of LTC$_4$ synthase; characterization of LTC$_4$ synthase would be important, notwithstanding the problems associated with its cloning.

SUMMARY OF THE INVENTION

Human leukotriene C$_4$ synthase (also referred to herein as "LTC$_4$ synthase") has been cloned in an expression cloning system using a highly sensitive assay for LTC$_4$, the product of the reaction catalyzed by LTC$_4$ synthase. According to one aspect of the invention, an isolated nucleotide sequence encoding a human leukotriene C$_4$ synthase polypeptide or unique fragments of human leukotriene C$_4$ synthase polypeptide, is provided. One embodiment is an isolated DNA sequence encoding a human leukotriene C$_4$ synthase polypeptide that has three hydrophobic transmembrane domains. Additionally, the invention relates to mammalian leukotriene C$_4$ synthase nucleotide sequences isolated from murine, porcine, ovine, bovine, feline, equine, or canine, as well as primate (e.g. simian) sources.

Also provided are recombinant cells and plasmids containing the foregoing isolated DNA, preferably linked to a promoter. Portions of the foregoing nucleotide sequences are also included in the invention. One such portion is contained in a vector within a host cell.

According to another aspect of the invention, isolated human leukotriene C$_4$ synthase polypetide is provided, having three hydrophobic transmembrane domains. Portions of the foregoing isolated human leukotriene C$_4$ synthase polypeptides are also included in the invention. Antibodies with selective binding specificity for the polypeptides of the invention also are provided.

Another aspect of the invention is a method for producing human leukotriene C$_4$ synthase polypeptide. The method includes providing an expression vector to a host, the vector containing a DNA sequence of the invention encoding for human leukotriene C$_4$ synthase polypeptide, allowing the host to express the human leukotriene C$_4$ synthase polypeptide, and isolating the expressed polypeptide.

A further aspect of the invention is an isolated nucleotide sequence capable of hybridizing to a target nucleotide sequence encoding human leukotriene C$_4$ synthase polypeptide. The target includes a nucleotide sequence encoding a human leukotriene C$_4$ synthase polypetide with three transmembrane domains. The nucleotide sequence also can encode a human leukotriene C$_4$ synthase polypeptide having amino acid sequences unique to the polypeptide.

The novel molecules of the invention can be employed in experimental or therapeutic protocols. For example, a method for interfering with the activity of a human leukotriene C$_4$ synthase gene is provided, in which a construct is arranged to include a human leukotriene C$_4$ synthase nucleotide sequence that, when inserted into the genome of a cell, either inactivates transcription of messenger RNA for human leukotriene C$_4$ synthase polypeptide and/or inactivates translation of messenger RNA into human leukotriene C$_4$ synthase polypeptide in that cell. This construct further has a promotor operatively liked to the leukotriene C$_4$ sequence. Next, the construct is introduced into a cell, and the construct is allowed to recombine with complementary sequences of the cell genome. Finally, cells lacking the ability to express human leukotriene C$_4$ synthase polypeptide are selected.

A further aspect of the invention is an assay method for identifying a modulator of a human leukotriene C$_4$ synthase polypeptide. The method includes providing a target cell containing an isolated nucleotide sequence which encodes for a human leukotriene C$_4$ synthase polypeptide. The target cell is maintained under conditions and for a time sufficient for the synthase to be expressed in the target cell. The target cell is then exposed to a compound suspected of modulating human leukotriene C$_4$ synthase polypeptide activity and a property of the target cell is measured in the presence of the modulator. This property is also measured in an identical target cell in the absence of the modulator. An altered property of the target cell exposed to the modulator is indicative of a modulating effect of the compound.

A highly sensitive assay for $LTC_4$, the product of the reaction catalyzed by $LTC_4$ synthase, is also described which includes the steps of contacting a carrier having bound to it an amount of an $LTC_4$ analogue (e.g., $LTC_2$) and incubating the carrier in the presence of a solution containing an unknown amount of leukotriene $C_4$ synthase. Next, the carrier and solution are contacted with an amount of anti-leukotriene $C_4$ antibody under conditions and for a time sufficient for the anti-leukotriene $C_4$ antibody to bind with leukotriene $C_4$ in solution and with analogue ($LTC_2$) on the carrier. Unbound anti-leukotriene $C_4$ antibody is separated from the carrier and then the carrier is contacted with a second antibody linked to a fluorescent label under conditions and for a time sufficient for the second antibody to bind with anti-leukotriene $C_4$ antibody associated with the carrier. The unbound second antibody is separated from the carrier and cell surface fluorescence of the carrier is analyzed by flow cytometry.

BRIEF DESCRIPTION OF THE FIGURES

FIG. 2 is the deduced amino acid sequence of human leukotriene $C_4$ synthase (SEQ ID NO. 2) based upon the sequence of FIG. 1.

BRIEF DESCRIPTION OF THE SEQUENCES

Figure 1A:
FIG. 1 is the nucleotide sequence of human leukotriene $C_4$ synthase (SEQ ID NO. 1)

SEQ ID NO.: 1 is the isolated cDNA sequence of human leukotriene $C_4$ synthase;

SEQ ID NO.: 2 is the deduced amino acid sequence of human leukotriene $C_4$ synthase based upon SEQ ID NO.: 1;

SEQ ID NO.: 3 (VSPPLTTGPPEFER) is a 14 amino acid sequence that is an internal tryptic fragment of native leukotriene $C_4$ synthase;

SEQ ID NO.: 4 (AGCGTTCCCCAGCTCGCCTTC) and SEQ ID NO.: 5 (CGGTCACTAGAACTTTAATGATAGAG) are a pair of oligonucleotide primers for PCR amplification of the human leukotriene $C_4$ synthase gene;

SEQ ID NOS. 6,7 and 8 are the three extramembrane ("loop") amino acid sequences of SEQ ID NO.: 2;

SEQ IN NO.: 9 (MKDEVALLAAVTLLGVLLQAYF) is the N-terminal 22 amino acid sequence of leukotriene $C_4$ synthase purified from native KG-1 cells.

DETAILED DESCRIPTION OF THE INVENTION

The novel polypetide of the present invention, hereinafter called, "human leukotriene $C_4$ synthase polypeptide" is a 150-amino acid residue integral membrane protein with three hydrophobic transmembrane domains. The nucleotide sequence of the leukotriene $C_4$ synthase of the invention is a 694 base pair complementary DNA sequence which encodes for the functional $LTC_4$ synthase enzyme.

The nucleotide and amino acid sequences of the full length enzyme, the configuration and number of transmembrane hydrophobic domains, and the lack of homology to known sequences, define a unique nucleotide and polypeptide structure. In this regard, the term "homology or homologous" is necessarily defined relative to a comparsion between two sequences. Given the known pattern of codon degeneracy, any identity between two nucleotide sequences above the codon degeneracy "noise", is considered to be a "signal" of homology. Preferably, at least 50% identity of nucleotide sequence is indicative of a "homologous" sequence.

One embodiment of a human leukotriene $C_4$ synthase molecule, according to the invention, is the isolated nucleotide sequence shown in SEQ ID NO.: 1. "Isolated", when applied to the nucleotide sequences encoding the polypeptides of the present invention means an RNA or DNA polymer, portion of genomic nucleic acid, cDNA, or synthetic nucleic acid which, by virtue of its origin or manipulation: (i) is not associated with all of a nucleic acid with which it is associated in nature (e.g., is present in a host cell as a portion of an expression vector); or (ii) is linked to a nucleic acid or other chemical moiety other than that to which it is linked in nature; or (iii) does not occur in nature.

By "isolated" it is further meant a nucleic acid sequence: (i) amplified in vitro by, for example, polymerase chain reaction (PCR); (ii) synthesized by, for example, chemical synthesis; (iii) recombinantly produced by cloning; or (iv) purified, as by cleavage and gel separation.

SEQ ID NO.: 1 (see also FIG. 1) is a 694 base pair complementary DNA sequence encoding for leukotriene $C_4$ synthase that has been isolated from human myelocytic cells. An open reading frame of 450 base pairs is identified from nucleotides 55 to 505 (TGA stop codon) of SEQ ID NO.: 1 (FIG. 1) and predicts an amino acid sequence of 150 amino acids (SEQ ID NO.: 2-FIG. 2). Numbering of nucleotides follows the convention of starting with the first base pair (A) of SEQ ID NO.: 1 as base number 1; amino acid residues begin with the start codon (ATG-bases 55–57) as residue number 1.

The cDNA contains a 54 nucleotide, 5' non-translated region; 450 nucleotides of translated sequence; an 193 nucleotide, 3' untranslated region that includes an ATTAAA polyadenylation signal (in bold lettering in FIG. 1), and a poly+ A tail (72 base pairs long—not shown in FIG. 1) indicating its full length. The cDNA sequence of SEQ ID NO.: 1 shows no significant homology with nucleotide sequences in GENBANK of EMBL databanks (using Molecular Biology Computer Research Resources (MBCR) software) for known cytosolic or microsomal GSH-S transferases. SEQ NO.: 1 encodes for a 150 amino acid residue protein with a calculated molecular weight and isoelectric point (pI) of 16,567 and 11.05, respectively. SEQ NO.: 1 is identical to two other clones having $LTC_4$ synthase activity (see Example 1). SEQ ID NO.: 1 was deposited with GENBANK and has been given GENBANK Accession Number U09353.

Another embodiment of the human $LTC_4$ synthase of the invention is the deduced, isolated amino acid sequence encoded by SEQ ID NO.: 1. The isolated polypeptide is given in SEQ ID NO. 2. The term "isolated", when applied to the polypeptides of the present invention means polypeptides: (i) encoded by nucleic acids using recombinant DNA methods; or (ii); synthesized by, for example, chemical synthetic methods; or (iii) separated from naturally-occurring biological materials, and then purified using protein analytical procedures; or (iv) associated with chemical moieties (e.g. polypeptides; carbohydrates, fatty acids, and the like) other than those associated with the polypeptide in its naturally-occurring state; or (v) that do not occur in nature. SEQ ID NO.: 2 contains 2 cysteine residues (residues 56 and 82), and two putative protein kinase phosphorylation sites (residues 28–30 and 111–113).

A search of protein sequence databases (SWISSPROT and PIR using BLAST™ and MBCRR software), relative to the deduced amino acid sequence of SEQ ID NO.: 2 reveals that SEQ ID NO.: 2 shares 31 percent overall homology with the 5-lipoxygenase activating protein (FLAP- see Dixon et al., Nature 343: 282–284 (1990)). This homology increases to 44 percent between the N-terminal two thirds of SEQ ID NO.: 2 (residues 4–97) and the N-terminal end of FLAP (amino acids 9–101). Within this N-terminal region, there are portions of near identity at residues 7–13 of $LTC_4$ (6 of 8 residues identical) and residues 46–52 of $LTC_4$ (6 of 7 residues identical). Alignment of the coding nucleotide sequence according to regions of amino acid homology reveals 52 percent homology between FLAP and $LTC_4$ in this N-terminal region. There is no nucleotide homology at the 3' end of the transcript for $LTC_4$ and the corresponding region of FLAP. FLAP then extends for an additional 300 base pairs.

A hydropathy analysis of the leukotriene $C_4$ synthase (Kyte, J. and R. Doolittle, J. Molec. Biol., 157: 105–132, 1982) of SEQ ID NO.: 2 was performed using a window of 6 amino acids. Briefly, a hydropathy analysis progressively evaluates the hydrophilic and hydrophobic properties of a protein as a scan along its amino acid sequence. There is a singular correspondence between interior portions of soluble, globular proteins and hydrophobicity, and a correspondence between exterior portions and hydrophilicity.

The hydropathy analysis reveals three potential transmembrane domains. Potential membrane spanning (hydrophobic) regions extend between amino acid residues 5–24, 59–89, and 114–135. The terms "hydrophilic and hydrophobic" in this context are primarily a function of the size of the amino acid "window" used in the hydropathy analysis. For the present purposes, "hydrophilic" refers to a stretch of amino acid sequences at least 20 residues long and scoring less than 0 on a Kyte-Doolittle plot; the scores are derived using a window of preferably at least 6 amino acids.

Native $LTC_4$ synthase protein from myelocytic KG-1 cells was solubilized, purified and sequenced. (See Example 1). In addition, recombinant $LTC_4$ protein derived from transfected COS-7 cells was purified and analysed using SDS-PAGE electrophoresis. (See Example 1). The predicted molecular weight of 16,567 for SEQ ID NO. 2 is in agreement with the observed mobility (18 kDa) of a native integral membrane protein. Furthermore, recombinant $LTC_4$ synthase purified from transfected cells also shows a molecular weight of approximately 18 kDa on SDS-PAGE. Furthermore, SEQ ID NO.: 2 matched the N-terminal 22 amino acids of the $LTC_4$ protein isolated and sequenced from KG-1 cells (SEQ ID NO.: 9) and 14 of 14 internal amino acids (SEQ ID NO.: 3) from tryptic fragments of the native protein. These 14 amino acids were identical to amino acid residues 35–48 of SEQ ID NO.: 2. SEQ ID NO.: 2 also matched 34 of 35 N-terminal amino acids purified from human leukemic THP-1 cell line. See Nicholson et al., Proc. Nat. Acad. Sci. USA, 90: 2015–2019 (1993).

Using the nucleotide sequence information provide in SEQ ID NO. 1, cell lines expressing the polypeptide of SEQ ID NO.: 2 can be established (Example 3). Likewise, homologues to SEQ ID NO.: 1 from other mammalian species can be identified using conventional techniques, described in greater detail below. Such genetic engineering techniques are well within the scope of those of ordinary skill in the art.

Northern blot analysis was employed to study steady state transcription of $LTC_4$ synthase and its distribution in human eosinophils and the KG-1 cell line. A 0.7 kb mRNA transcript was observed in these cells, both of which are known to contain $LTC_4$ synthase. The size of the mRNA (0.7 kb) is similar to that of SEQ ID NO.1, consistent with SEQ ID NO.: 1 being full length. (see Example 1).

A nucleotide sequence encoding leukotriene $C_4$ synthase has been cloned, isolated and expressed. A general protocol is presented below. This protocol is intended to obtain a cDNA having a complete reading frame for the polypeptide.

A. Cloning Human Leukotriene $C_4$ Synthase Polypeptide

A cDNA encoding leukotriene $C_4$ synthase is cloned by expressing a leukotriene $C_4$ synthase from a cDNA expression library in mammalian COS-7 cells. (See Example 1). Briefly, mRNA is isolated from cells containing $LTC_4$ synthase. Next, mRNA is used to prepare a cDNA library using an in vitro expression vector system. cDNA is synthesized, separated by gel electrophoresis and ligated into an expression vector. This synthetic cDNA library is used to transform a bacterial host and bacteria are then subjected to extraction of their plasmid cDNA. Plasmids are used to transfect mammalian cells. The cDNA library was screened for expression of $LTC_4$ synthase in transfectants by a highly sensitive, fluorescence-linked competitive immunoassay (See Example 1).

For sequencing, plasmid cDNA from the clones is extracted, then cloned into a vector for DNA sequencing, using standard methods. See for example, Sambrook, J. et al., Molecular Cloning, Cold spring Harbor Press, N.Y. See also, Example 1.

B. Cloning Other Homologues of Human Leukotriene $C_4$ Synthase Polypeptide

Now that the cDNA sequence of human leukotriene $C_4$ synthase has been characterized, one can use a variety of approaches for cloning other human homologues. One approach used to screen a DNA library for the presence of a human leukotriene $C_4$ synthase nucleotide coding sequence corresponding to a human homologue includes generating preferred probes using the polymerase chain reaction. The probes are produced by using, for example, a human granulocyte or myelocytic cell line (i.e., KG-1, THP-1) cDNA library as a template for polymerase chain reaction (PCR). Based on the degree of codon degeneracy of the predicted amino acid sequence, PCR primers are derived from the human leukotriene $C_4$ synthase nucleotide sequence of SEQ ID NO.: 1. Examples of suitable PCR primer pairs include SEQ ID NO.: 4 (AGCGTTCCCCAGCTCGCCTTC) and SEQ ID NO.: 5 (CGGTCACTAGAACTTTAATGATAGAG). See Example 2.

The product of the PCR reaction is cloned and the human cDNA library is rescreened using the PCR product as the probe(s). This preferred method, however, requires identifying tissue that expresses leukotriene $C_4$ synthase as a source of RNA.

Other tissues suspected of expressing the human homologue can, however, be identified by RNA analysis, i.e., Northern blot analysis under low stringency conditions. Confirmation of a human tissue as an RNA source and identification of additional sources of tissue can be accomplished by preparing RNA from the selected tissue and performing Northern blot analysis under low stringency conditions using PCR product as the probe(s). A suitable range of such stringency conditions is described in Krause, M. H., and Aaronson, S. A., 1991, Methods in Enzymology 200: 546–556. Additionally, genomic libraries can be screened for the presence of the human homolog coding sequence using a PCR generated probe(s).

C. Testing and Cloning Related Molecules

The invention also pertains to a more general protocol for isolating the gene for leukotriene $C_4$ synthase. In this approach, total mRNA can be isolated from mammalian tissues or from cell lines likely to express leukotriene $C_4$ synthase polypeptide. In general, total RNA from the selected tissue or cell culture is isolated using conventional methods. Subsequent isolation of mRNA is typically accomplished by oligo (dT) chromatography. Messenger RNA for Northern analysis is size-fractionated by electrophoresis and the RNA transcripts are transferred to nitrocellulose according to conventional protocols (Sambrook, J. et al., Molecular Cloning, Cold spring Harbor Press, N.Y.).

A labelled PCR-generated probe capable of hybridizing with the human leukotriene $C_4$ synthase nucleotide (SEQ ID NO.: 1) can serve to identify RNA transcripts complementary to at least a portion of the human leukotriene $C_4$ synthase gene. For example, if Northern analysis indicates that RNA isolated from murine lung tissue hybridizes with the labelled probe, then a murine lung cDNA library is a likely candidate for screening and identification of a clone containing the coding sequence for a murine homolog of human leukotriene $C_4$ synthase polypeptide.

Northern analysis is used to confirm the presence of mRNA fragments which hybridize to a probe corresponding to all or part of the human leukotriene $C_4$ synthase polypeptide. Northern analysis indicates the presence and size of the transcript. This allows one to determine whether a given cDNA clone is long enough to encompass the entire transcript or whether it is necessary to obtain further cDNA clones, i.e., if the length of the cDNA clone is less than the length of RNA transcripts as seen by Northern analysis. If the cDNA is not long enough, it is necessary to perform several steps such as: (i) rescreen the same library with the longest probes available to identify a longer cDNA; (ii) screen a different cDNA library with the longest probe; and (iii) prepare a primer-extended cDNA library using a specific nucleotide primer corresponding to a region close to, but not at, the most 5' available region. This nucleotide sequence is used to prime reverse transcription. The primer extended library is then screened with the probe corresponding to available sequences located at 5' to the primer. See for example, Rupp et al., Neuron, 6: 811–823 (1991).

The preferred clone of leukotriene $C_4$ synthase has a complete coding sequence, i.e., one that begins with methionine, ends with a stop codon, and preferably has another in-frame stop codon 5' to the first methionine. It is also desirable to have a cDNA that is "full length", i.e. includes all of the 5' and 3' untranslated sequences. To assemble a long clone from short fragments, the full-length sequence is determined by aligning the fragments based upon overlapping sequences. Thereafter, the full-length clone is prepared by ligating the fragments together using the appropriate restriction enzymes.

As discussed above, PCR-generated probes may be used in the protocol for isolating mammalian homologues to human leukotriene $C_4$ synthase polypeptide. Moreover, probes to be used in the general method for isolating mammalian leukotriene $C_4$ synthase can now include oligonucleotides, all of which encode at least part of the sequence shown in SEQ ID NO.: 1. Unlike the PCR approach to generating a probe, the above-identified probes do not require prior isolation of RNA from a tissue expressing the vertebrate homolog.

An oligodeoxyribonucleotide probe typically has a sequence somewhat longer than that used for the PCR primers. A longer sequence is preferable for the probe, and it is important that codon degeneracy be minimized. A representative protocol for the preparation of an oligonucleotide probe for screening a cDNA library is described in Sambrook, J. et al., Molecular Cloning, Cold Spring Harbor Press, New York, 1989. In general, the probe is labelled, e.g., with $^{32}P$, and used to screen clones of a cDNA or genomic library.

Alternately, an expression library can be screened using conventional immunization techniques, such as those descried in Harlowe and Lane, D. (1988), Antibodies, Cold Spring Harbor Press, New York. Antibodies prepared using purified leukotriene $C_4$ synthase as an immunogen are preferably first tested for cross reactivity with the homolog of leukotriene $C_4$ synthase from other species. Other approaches to preparing antibodies for use in screening DNA libraries, as well as for use in diagnostic and research applications, are described below. See Example 3.

D. Nucleic Acid and Protein Sequences

The nucleic acid sequence of the human leukotriene $C_4$ synthase is depicted in SEQ ID NO.: 1. This sequence, its functional equivalents, or fragments of this sequence may be used in accordance with the invention. The term "fragments" refers to portions of the human leukotriene $C_4$ synthase nucleic acid sequence that may find no counterpart in the known sequences of other polypeptides. Subsequences comprising hybridizable portions of the $LTC_4$ synthase sequence have use, e.g., in nucleic acid hybridization assays, Southern and Northern blot analyses, etc.

Exemplary nucleotide subsequences of SEQ ID NO.: 1 are those encoding extramembrane, "loop" portions of $LTC_4$ synthase, such as nucleotide sequences or portions of nucleotide sequences encoding (with reference to the residues of SEQ ID NO.: 2) amino acid residues 25 to 58 (SEQ ID NO.: 6); amino acid residues 90 to 113 (SEQ ID NO.: 7); and amino acid residues 136 to 150 (SEQ ID NO.: 8).

Moreover, the nucleic acid sequence depicted in SEQ ID NO: 1 can be altered by mutations such a substitutions, additions or deletions that provide for functionally equivalent nucleic acid sequences. According to the present invention, a nucleic acid sequence is "functionally equivalent" compared with the nucleic acid sequence depicted in SEQ ID NO.: 1, if it satisfies at least one of the following conditions: (i) the nucleic acid sequence has the ability to hybridize to a human leukotriene $C_4$ synthase nucleotide sequence, but it does not necessarily hybridize to that sequence with an affinity that is the same as that of the naturally occurring human leukotriene $C_4$ synthase nucleic acid sequence; and/or (ii) the nucleic acid can serve as a probe to distinguish between the present human leukotriene $C_4$ synthase sequences and other nucleotide sequences.

The term "probe", therefore, refers to a ligand of known qualities that can bind selectively to a target. As applied to the nucleic acid sequences of the invention, the term "probe" refers to a strand of nucleic acid having a base sequence complementary to a target sequence. Preferred nucleotide sequences may hybridize if they contain sequences that have at least 50% identity to a target sequence. A preferred probe that can distinguish between a human leukotriene $C_4$ synthase sequence and other sequences refers to a probe that includes SEQ ID NO.: 1, functional variants, or fragments thereof.

Because the nucleic acid sequence of leukotriene $C_4$ synthase is now known, those of ordinary skill in the art can readily determine nucleic acid sequences of the human leukotriene $C_4$ synthase that are not homologous to any other nucleic acid sequence, including other human leukotriene $C_4$ synthase sequences. These non-homologous sequences, and peptides encoded by them, are referred to as "unique" fragments and are meant to be included within the scope of the present invention.

Moreover, due to the degeneracy of nucleotide coding sequences, other nucleic acid sequences may be used in the practice of the present invention. These include, but are not limed to, sequences comprising all or portions of the human leukotriene $C_4$ synthase sequences depicted in SEQ ID NO.: 1 which are altered by the substitution of different codons that encode the same amino acid residue within the sequence, thus producing a silent change. Such altered sequences are regarded as equivalents of the specifically claimed sequences.

Human leukotriene $C_4$ synthase polypeptide or fragments or other derivatives thereof include, but are not limited to, those containing as a primary amino acid sequence all, or unique parts of the amino acid residues substantially as depicted in SEQ ID NO.: 2, including altered sequences in which functionally equivalent amino acid residues are substituted for residues within the sequence, resulting in a silent change. According to the invention, an amino acid sequence is "functionally equivalent" compared with a sequence depicted in SEQ ID NO.: 2 if the amino acid sequence contains one or more amino acid residues within the sequence which can be substituted by another amino acid of a similar polarity which acts as a conservative substitution (i.e., a functional equivalent). For example, at least one of the tyrosine residues at positions 50, 93 and 109 of SEQ ID NO. 2 may be substituted by a phenylalanine, yielding a total of $2^3$ or 8 separate functional equivalents of SEQ ID NO.: 2.

In addition, substitutes for an amino acid within the sequence may also be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Substantial changes in functional or, for example, immunological properties may be made by selecting substitutes that differ from the original amino acid residue. More significantly, the substitutions are chosen for their effect on: (i) maintaining the structure of the peptide backbone in the area of the substitution, for example, as a sheet or helical conformation; (ii) maintaining the charge or hydrophobicity of the molecule at the target side; or (iii) maintaining the bulk of the side chain.

The substitutions that in general are expected to induce greater changes in the functional properties of $LTC_4$ synthase are those in which: (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl, or (e) a residue having a bulky side chain, e.g., phenylalanine, is substituted for one (or by) one not having such a side chain, e.g., glycine.

In particular, any change in the number of arginine residues will have an effect on the isoelectric point (pI) of the $LTC_4$ synthase. Arginine has the highest pI (10.76) of all the standard amino acids. Fewer arginine residues would be expected to result in an $LTC_4$ synthase with a lower pI and may be expected to result in an enzyme with reduced activity. Substitution of an arginine residue of SEQ ID NO.: 2 with an aspartic acid (pI=2.77) is a particularly effective substitution for lowering the $LTC_4$ synthase isoelectic point. For example, SEQ ID NO.: 2 has 13 arginine residues at positions 30, 31, 34, 48, 51, 90, 92, 99, 104, 113, 136, 142, and 144. Substitution of at least one aspartic acid for at least one of these arginines would yield a total of $2^{13}$ or 8192 separate modifications of SEQ ID NO.: 2.

In addition, substitution of at least one arginine residue with at least one glutamic acid (pI=3.22) is another substitution likely to lower the $LTC_4$ synthase isoelectric point. Substitution of at least one glutamic acid for at least one of these arginines would also yield a total of $2^{13}$ or 8192 separate modifications of SEQ ID NO.: 2. Synthesis of all of these sequences is well within the present level of skill in the art.

Most deletions and insertions in the human leukotriene $C_4$ synthase polypeptide, and substitutions in particular, are not expected to produce radical changes in the characteristics of the polypeptide. Nevertheless, when it is difficult to predict the exact effect of the substitution, deletion, or insertion in advance of doing so, one skilled in the art will appreciate that the effect will be evaluated using routine screening assays as described below. For example, a change in the immunological character of the human leukotriene $C_4$ synthase polypeptide, such as binding to a given antibody, is measured by an immunoassay such as a competitive type immunoassay.

Also included within the scope of the invention are human leukotriene $C_4$ synthase polypeptides or unique fragments or derivatives thereof which are differentially modified during or after translation, e.g., by phosphorylation, glycosylation, crosslinking, acylation, proteolytic cleavage, linkage to an antibody molecule, membrane molecule or other ligand, (Ferguson, et al., 1988, Ann. Rev. Biochem. 57:285–320).

In addition, the recombinant human leukotriene $C_4$ synthase polypeptide-encoding nucleic acid sequences of the invention may be engineered so as to modify processing or expression of the human leukotriene $C_4$ synthase polypeptide. For example, and not by way of limitation, the human leukotriene $C_4$ synthase nucleotide sequence(s) may be combined with a promoter sequence and/or a ribosome binding site using well characterized methods, and thereby facilitate harvesting or bioavailability.

Now that the cDNA of human $LTC_4$ synthase has been identified, it will be readily appreciated that the human leukotriene $C_4$ synthase nucleotide sequence can be mutated in vitro or in vivo, to create variations in coding regions and/or form new restriction endonuclease sites or destroy preexisting ones, to facilitate further in vitro modification. Any technique for mutagenesis known in the art can be used including, but not limited to, in vitro site-directed mutagenesis (Hutchinson, et al., 1978, J. Biol. Chem. 253:6551), use of TAB® linkers (Pharmacia), PCR-directed mutagenesis, and the like.

In addition to generating fragments of leukotriene $C_4$ synthase from expression of cloned partial sequences of human leukotriene $C_4$ synthase polypeptide DNA, fragments of human leukotriene $C_4$ synthase polypeptide can be generated directly from the intact polypeptide. Proteins are specifically cleaved by proteolytic enzymes, including, but not limited to, trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine. Alternate sets of cleaved polypeptide fragments are generated by preventing cleavage at a site which is susceptible to a proteolytic enzyme. For example, reaction of the ϵ-amino groups of lysine with ethyltrifluorothioacetate in mildly basic solution yields a blocked amino acid residue whose adjacent peptide bond is no longer susceptible to hydrolysis by trypsin (Goldberger et al. Biochem., 1:401 (1962)). Treatment of such a polypeptide with trypsin thus cleaves only at the arginyl residues.

Polypeptides also can be modified to create peptide linkages that are susceptible to proteolytic enzyme catalyzed hydrolysis. For example, alkylation of cysteine residues with β-halo ethylamines yields peptide linkages that are hydrolyzed by trypsin (Lindley, Nature, 178: 647 (1956)). In addition, chemical reagents that cleave polypeptide chains at specific residues can be used (Withcop, Adv. Protein Chem. 16: 221 (1961)). For example, cyanogen bromide cleaves polypeptides at methionine residues (Gross & Witkip, J. Am Chem Soc., 83: 1510 (1961)). Thus, by treating leukotriene $C_4$ synthase or fragments thereof with various combinations of modifiers, proteolytic enzymes and/or chemical reagents, numerous discrete overlapping peptides of varying sizes are generated. These peptide fragments can be isolated and purified from such digests by chromatographic methods.

Alternatively, human leukotriene $C_4$ synthase polypeptides can be synthesized using an appropriate solid state synthetic procedure (Steward and Young, *Solid Phase Peptide Synthesis*, Freemantle, San Francisco, Calif. (1968)). A preferred method is the Merrifield process (Merrifield, *Recent Progress in Hormone Res.*, 23: 451 (1967)). The activity of these peptide fragments may conveniently be tested using, for example, a COS-7 expression assay as described herein.

The human leukotriene $C_4$ synthase sequences of the invention also include non-human homologues of the amino acid sequence of SEQ ID NO.: 2. The non-human leukotriene $C_4$ synthases of the invention may be prepared by recombinant nucleic acid expression techniques or by chemical synthesis using standard peptide synthesis techniques.

Also within the scope of the invention are nucleic acid sequences or proteins encoded by nucleic acid sequences derived from the same gene but lacking one or more structural features as a result of alternative splicing of transcripts from a gene that also encodes the complete human leukotriene $C_4$ synthase polypeptide gene, as defined previously.

Nucleic acid sequences complementary to DNA or RNA sequences encoding leukotriene $C_4$ synthase or a functionally active portion(s) thereof are also provided. In animals, particularly transgenic animals, RNA transcripts of a desired gene or genes may be translated into polypeptide products having a host of phenotypic actions.

In a particular aspect of the invention, antisense oligonucleotides and oligonucleotide analogs can be synthesized. Antisense oligonucleotides or analogs specifically bind to the complementary sequence of either pre-mRNA or mature mRNA, as defined by Watson-Crick base pairing, inhibiting the flow of genetic information from DNA to protein. These oligonucleotides may have activity in their own right, such as antisense reagents which block translation or inhibit RNA function. Where leukotriene $C_4$ synthase is to be produced utilizing the nucleotide sequences of this invention, the DNA sequence may also be in an inverted orientation which gives rise to a negative sense RNA on transcription. This RNA is not capable of being translated to the desired human leukotriene $C_4$ synthase polypeptide product, as it is in the wrong orientation and would give a nonsensical product if translated, thus modulating production of $LTC_4$ synthase. In this regard, "oligonucleotide" refers to a polynucleotide formed from naturally occurring bases and cyclofuranasyl groups joined by phosphodiester bonds. "Oligonucleotide analog", refers to moieties which function similarly to anti-sense oligonucleotides but which have non-naturally-occurring portions which are not closely homologous. Thus, oligonucleotides may have altered sugar moities or inter-sugar linkages. Exemplary are phosphorothioate and other sulfur linkages species known in the art. Such analogs are functional equivalents of the anti-sense oligonucleotides of the invention. The most direct effect which antisense oligonucleotides have on intact cells that can be easily quantified is specific inhibition of $LTC_4$ synthase activity (See Example 1).

E. Expression of Polypeptide

The present invention also permits the expression, isolation, and purification of the human leukotriene $C_4$ synthase polypeptide. A human leukotriene $C_4$ synthase nucleotide sequence may be cloned or subcloned using any method known in the art. It will be appreciated that some post-transitional events such as glycosylation, phosphorylation, and/or subunit assembly may not be carried out in the same manner in all eukaryotic cells. The preferred expression systems utilize mammalian cells and cell lines. A large number of vector-mammalian host systems known in the art may be used. Possible vectors include, but are not limited to, cosmids, plasmids or modified viruses, but the vector system must be compatible with the host cell used. Viral vectors include, but are not limited to, vaccinia virus, or lambda derivatives. Plasmids include, but are not limited to, pBR322, pUC, or Bluescript® (Stratagene) plasmid derivatives. Recombinant human leukotriene $C_4$ synthase polypeptide molecules can be introduced into host cells via transformation, transfection, infection, electroporation, etc. Generally, introduction of human leukotriene $C_4$ synthase polypeptide molecules into a host is accomplished using a vector containing human leukotriene $C_4$ synthase polypeptide DNA under control by regulatory regions of the DNA that function in the host cell.

In one method of expressing human leukotriene $C_4$ synthase polypeptide, the cDNA that corresponds to the entire coding region (SEQ ID NO.: 1) is moved by way of a eukaryotic expression vector into cells derived from the simian kidney (e.g., COS-7 cells). Expression is monitored after transfection by measuring the production of $LTC_4$. See Examples 1 and 3. The details of this experimental approach for transfection, selection and characterization of the leukotriene $C_4$ synthase are similar to those that have been used previously for other polypeptides (see, for example, Birnir, B. et al., Biochim. Biophys. Acta, 1048: 100–104 (1990), the entire contents of which are incorporated herein by reference.

Once the polypeptide is expressed, it may be isolated and purified by standard methods including chromatography (e.g., ion exchange, affinity, and sizing column chromatography), centrifugation, differential solubility, or by any other standard technique for the purification of proteins. In particular, leukotriene $C_4$ synthase may be isolated by binding to an affinity column comprising antibodies to leukotriene $C_4$ synthase bound to a stationary support.

F. Preparation of Antibodies to the Polypeptide

The term "antibodies" is meant to include monoclonal antibodies, polyclonal antibodies and antibodies prepared by recombinant nucleic acid techniques that are selectively reactive with human leukotriene $C_4$ synthase polypeptide. The term "selectively reactive" refers to those antibodies that react with one or more antigenic determinants of human leukotriene $C_4$ synthase polypeptide, and do not react with other transporter polypeptides. Determinants usually consist of chemically active surface groupings of molecules such as amino acids or sugar side chains and have specific three dimensional structural characteristics as well as specific charge characteristics. Antibodies include those raised against the human polypeptide of SEQ ID NO.: 2 and intended to cross-react with other human homologs but not with non-human $LTC_4$ synthase. These antibodies may be useful for diagnostic applications. Other antibodies include those raised against non-human (i.e., mouse or goat) leukotriene $C_4$ synthase, which antibodies may be generally used for research purposes. These antibodies include those raised against short, synthetic peptides of the non-human sequence.

Antibodies may be raised against human $LTC_4$ synthase and isolated by standard protein purification methods. Generally, a peptide immunogen is first attached to a carrier to enhance the immunogenic response. Although the peptide immunogen can correspond to any portion of the amino acid sequence of the human leukotriene $C_4$ synthase or to variants of the sequence, such as the amino acid sequences corresponding to the primers and probes described, certain peptides are more likely than others to provoke an immediate response. For example, a peptide including the C-terminal amino acid is more likely to generate an antibody response.

Other alternatives to preparing antibodies reactive with human $LTC_4$ synthase include: immunizing an animal with a protein expressed by a procaryotic (e.g., bacterial) or eucaryotic cell, which cell includes the coding sequence for: (i) all or part of human $LTC_4$ synthase; or (ii) the coding sequence for all or part of a non-human (i.e., mouse) leukotriene $C_4$ synthase. Antibodies can also be prepared by immunizing an animal with whole cells that are expressing all or a part of a cDNA encoding the human leukotriene $C_4$ synthase polypeptide. For example, cDNA encoding the leukotriene $C_4$ synthase of the present invention (e.g., SEQ ID NO.: 1) may be expressed in a host using standard techniques (see Sambrook et al., Molecular Cloning; A Laboratory Manual, Cold Spring Harbor Press, Cole Spring Harbor, N.Y. (1989) or methods described herein such that 5–20% of the total of protein recovered is human leukotriene $C_4$ synthase polypeptide. Proteins are electrophoresed using PAGE, the appropriate band cut, the protein eluted, and prepared for immunization. Mice are immunized twice intraperitoneally with 50 micrograms protein immunogen per mouse. Their sera is tested for antibody activity by immunohistology or immunocytology on any leukotriene $C_4$ synthase expressing cell system (e.g., transfected COS-7 cells) and/or by immunoassay with the expressed human leukotriene $C_4$ synthase polypeptide. For immunohistology, a biotin-conjugated anti-mouse immunoglobulin may be used followed by avidin-peroxidase, and a chromogenic peroxidase substrate. Such preparations are commercially available; for example, from Zymad Corp., San Francisco, Calif. Animals with serum antibodies are sacrificed three days later and their spleens taken for fusion and hybridoma production, as above. Positive supernatants are tested as above and by, for example, Western blot analysis.

To further improve the likelihood of producing an anti-human leukotriene $C_4$ synthase immune response, the amino acid sequence of the leukotriene $C_4$ synthase may be analyzed in order to identify portions of the molecule which may be associated with increased immunogenicity. For example, the amino acid sequence may be subjected to computer analysis to identify surface epitopes which present computer-generated plots of antigenic index, an amphophilic helix, amphophilic sheet, hydrophilicity, and the like. Alternatively, the deduced amino acid sequences of leukotriene $C_4$ synthase from different species could be compared, and relatively non-homologous regions identified. These non-homologous regions would be more likely to be immunogenic across various species.

For preparation of monoclonal antibodies directed toward human leukotriene $C_4$ synthase polypeptide, any technique which provides for the production of antibody molecules by continuous cell lines and culture may be used. For example, the hybridoma technique originally developed by Kohler and Milstein (Nature, 256: 495–497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to form anti-human leukotriene $C_4$ synthase antibodies (Ladner et al. U.S. Pat. Nos. 4,946,778 and 5,260,203). Recent developments in production of human monoclonal antibodies, involving insertion of human heavy and light-chain genetic loci into mice in which endogenous production of heavy and light chains is disrupted, has lead to mice that can synthesize human antibodies specific for human antigens, and can be employed to produce hybridomas making human antibodies. See, Lonberg, et al., Nature 368: 856–859 (1994) and Green et al., Nature Genet., 7: 13–21 (1994), incorporated herein by reference.

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to anti-human leukotriene $C_4$ synthase polypeptide monoclonal antibodies or other molecules of the invention. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retains their respective activities. This linkage can include many chemical mechanisms, for instance covalent binding, affinity binding, intercalation, coordinate binding and complexation. The preferred binding is, however, covalent binding. The covalent binding can be achieved either by direct condensation of existing side chains or by the incorporation of external bridging molecules. Many bivalent or polyvalent linking agents are useful in coupling protein molecules, such as an anti-human leukotriene $C_4$ synthase monoclonal antibody, to other molecules. For example, representative coupling agents can include organic compounds such as thioesters, carbodiimides, succinimide ester, diisocyanates, gluteraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." Jour. Immun. 133:1335–2549; Jansen, F. K., H. E. Blythman, D. Carriere, P. Casella, O. Gros, P. Gros, J. C. Invent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185–216; and Vitetta et al., supra).

Preferred linkers are described in the literature. See, for example, Ramakrishnan, S. et al., Cancer Res. 44:201–208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. #21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In other embodiments, compositions of the invention can be used as reagents in immunoassays to detect antibodies against human leukotriene $C_4$ synthase. Immunoassays can be any of the conventional assay types. For example, a sandwich assay can be performed in which the leukotriene $C_4$ synthase of the invention is affixed to a solid phase. A liquid sample such as bronchial fluid containing, or suspected of containing, antibodies directed against leukotriene $C_4$ synthase is incubated with the solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid phase and the label bound to the solid phase is measured, the amount of the label detected serving as a measure of the amount of anti-human leukotriene $C_4$ synthase antibody present in the sample. These and other immunoassays can be easily performed by those of ordinary skill in the art using the present compositions as reagents. Such fragments are typically produced by proteolytic cleavage using enzymes such a papain or pepsin, using methods well known in the art.

Radioactive isotopes can be detected by such means as the use of a gamma counter or assimilation counter or by autoradiography. For example, reference by Work, T. S. et al., laboratory techniques and biochemistry and molecular biology, North Holland Publishing Company, New York 1978.

G. Assays/Utilities

The present invention provides for assay systems in which activity or activities resulting from exposure to a peptide or non-peptide compound may be detected by measuring a physiological response to the compound in a cell or cell line which expresses the molecules of the invention. A "physiological response" may comprise any biological response, including but not limited to transcriptional activation of certain nucleic acid sequences (e.g.. promoter/enhancer elements as well as structural genes), translation, or phosphorylation, or the induction of human leukotriene $C_4$ synthesis.

The present invention thus provides for the development of novel assay systems which may be utilized in the screening of compounds directed against human leukotriene $C_4$ synthase. Target cells expressing human leukotriene $C_4$ synthase polypeptide, which are modulated (i.e., activated and/or inhibited) by the compounds, may be produced by transfection with human leukotriene $C_4$ synthase polypeptide-encoding nucleic acid.

A convenient assay method for identifying a modulator of a human leukotriene $C_4$ synthase polypeptide includes providing a human leukotriene $C_4$ synthase messenger RNA to a target cell such as an mammalian COS-7 cell; incubating the cell in the presence of the modulating compound; and measuring synthesis of the product of the $LTC_4$ synthase reaction ($LTC_4$). Alternately, one could measure expression of the messenger RNA into the human leukotriene $C_4$ synthase polypeptide using the sensitive $LTC_4$ synthase assay described herein. In particular, one can screen many compounds of interest in a short period of time using this sensitive $LTC_4$ synthase assay.

An exemplary assay method for identifying a modulator of a human leukotriene $C_4$ synthase polypeptide may include providing a target cell containing an isolated nucleotide sequence which encodes for a human leukotriene $C_4$ synthase polypeptide; maintaining the target cell under conditions and for a time sufficient for the leukotriene $C_4$ synthase to be expressed in the target cell; exposing the target cell to a compound suspected of modulating leukotriene $C_4$ synthase activity; measuring a property of the target cell in the presence of the modulator; and comparing this property to that of a target cell in the absence of the modulator but containing the isolated nucleotide sequence. An altered property of the target cell exposed to the modulator is indicative of a modulating effect of the compound. Transfection of mammalian cell lines with eukaryotic DNA is well known and the techniques have been described extensively in the literature. See, for example Sambrook, J. et al., Molecular Cloning, Cold Spring Harbor Press, New York, 1989, the entire contents of which are incorporated herein by reference.

Once target cell lines are produced or identified, it may be desirable to select for cells which are exceptionally sensitive to a particular compound. Such target cells may express large amounts of human leukotriene $C_4$ synthase polypeptide. Target cells expressing a relative abundance of the polypeptide could be identified by selecting target cells which, when incubated with a compound/tag, produce a relatively higher degree of human leukotriene $C_4$ synthesis. Alternatively, cell lines which are exceptionally sensitive to a compound may exhibit a relatively strong biological response, such as a sharp increase in immediate early gene products such as c-fos or c-jun, in response to leukotriene $C_4$ synthase expression. By developing assay systems using target cells which are extremely sensitive to a compound, the present invention provides for methods of screening for low levels of human leukotriene $C_4$ synthase activity.

In particular, using recombinant DNA techniques, the present invention provides for human leukotriene $C_4$ synthase target cells which are engineered to be highly sensitive to modulating compounds. For example, the human leukotriene $C_4$ synthase gene, cloned according to the methods set forth above, may be inserted into cells which naturally express leukotriene $C_4$ synthase such that the recombinant human leukotriene $C_4$ synthase gene is expressed at high levels.

The present invention also provides for experimental model systems for studying the physiological role of the native human leukotriene $C_4$ synthase polypeptide. In these model systems, human leukotriene $C_4$ synthase polypeptide, peptide fragment, or a derivation thereof, may be either supplied to the system or produced within the system. Such model systems could be used to study the effects of human leukotriene $C_4$ synthase excess or depletion. The experimental model systems may be used to study the effects of increased or decreased response to ligand in cell or tissue cultures, in whole animals, or in particular cells or tissues within whole animals or tissue culture systems, or over specified time intervals (including during embryogenesis).

In additional embodiments of the invention, a human leukotriene $C_4$ synthase sequence may be used to inactivate the endogenous gene by homologous recombination, and thereby create a human leukotriene $C_4$ synthase-deficient cell, tissue, or animal. For example, and not by way of limitation, a recombinant human leukotriene $C_4$ synthase nucleotide sequence may be engineered to contain an insertional mutation (e.g., the neo gene) which, when inserted, inactivates transcription of human leukotriene $C_4$ synthase polypeptide. Such a construct, under the control of a suitable promoter operatively linked to the human leukotriene $C_4$ synthase nucleotide sequence, may be introduced into a cell by a technique such as transfection, transduction, injection, etc. In particular, stem cells lacking an intact human leukotriene $C_4$ synthase gene may generate transgenic animals deficient in human leukotriene $C_4$ synthase polypeptide. A "transgenic animal" is an animal having cells that contain DNA which has been artificially inserted into a cell, which DNA becomes part of the genome of the animal which develops from that cell. The preferred DNA encodes for leukotriene $C_4$ synthase and may be entirely foreign to the transgenic animal or may be homologous to the natural leukotriene $C_4$ synthase of the transgenic animal, but which is inserted into the animal's genome at a location which differs from that of the natural homolog.

In a specific embodiment of the invention (See Example 5), the endogenous human leukotriene $C_4$ synthase gene of a cell may be inactivated by homologous recombination with a mutant human leukotriene $C_4$ synthase gene to form a transgenic animal lacking the ability to express human leukotriene $C_4$ synthase polypeptide. In another embodiment, a construct can be provided that, upon transcription, produces an "anti-sense" nucleic acid sequence which, upon translation, will not produce the required human leukotriene $C_4$ synthase polypetide.

In a further embodiment of the invention, leukotriene $C_4$ synthase expression may be reduced by providing human leukotriene $C_4$ synthase polypeptide-expressing cells, preferably in a transgenic animal, with an amount of human leukotriene $C_4$ synthase polypeptide anti-sense RNA or DNA effective to reduce expression of human leukotriene $C_4$ synthase polypeptide.

A transgenic animal (preferably a non-human mammal) can also be provided with a human leukotriene $C_4$ synthase DNA sequence that also encodes a repressor protein that can bind to a specific DNA sequence of human leukotriene $C_4$ synthase polypeptide, thereby reducing ("repressing") the level of transcription of human leukotriene $C_4$ synthase DNA.

Transgenic animals of the invention which have attenuated levels of leukotriene $C_4$ synthase expression have general applicability to the field of transgenic animal generation, as they permit control of the level of expression of genes.

According to the present invention, human leukotriene $C_4$ synthase probes may be used to identify cells and tissues of transgenic animals which lack the ability to transcribe human leukotriene $C_4$ synthase nucleotide sequences. Leukotriene $C_4$ synthase expression may be evidenced by transcription of human leukotriene $C_4$ synthase mRNA or production of human leukotriene $C_4$ synthase polypeptide, determined using probes as described above. One variety of probe which may be used to detect human leukotriene $C_4$ synthase expression is a nucleic acid probe, containing at least a portion of SEQ ID NO.: 1. Detection of human leukotriene $C_4$ synthase-encoding mRNA may be easily accomplished by any method known in the art, including, but not limited to, in situ hybridization, Northern blot analysis, or PCR related techniques. Probes of SEQ ID NO.: 1 or derived therefrom, may be used to screen tissues of patients with, for example, asthma in order to detect the presence of aberrant leukotriene $C_4$ synthase encoding mRNA. Another variety of probe which may be used is an anti-human $LTC_4$ synthase antibody to screen patients for abnormal levels of the enzyme.

The above-mentioned probes may be used experimentally to identify cells or tissues which hitherto had not been shown to express human leukotriene $C_4$ synthase polypeptide. Furthermore, these methods may be used to identify the expression of $LTC_4$ synthase by aberrant tissues, such as malignancies.

Pharmaceutical Compositions

Those of ordinary skill in the art will recognize that modulators of human $LTC_4$ synthase may have potential therapeutic applications. The compositions and assays described herein, by modulating synthesis of LTC$_4$, can provide clinicians with strategies for the treatment of patients with inflammatory conditions such as cardiac ischemia, anaphylactic shock, cold-induced asthma, exercise-induced asthma, aspirin-induced asthma, and allergic rhinitis. Therefore, the development of drugs which selectively inhibit human leukotriene C$_4$ synthesis is expected to provide an important advantage. Full-length LTC$_4$ synthase, modulators of the synthase, functional equivalents, modifications, and/or nucleic acids capable of encoding them may be used in pharmaceutical compositions. An exemplary pharmaceutical composition comprises a therapeutically effective amount of active ingredient(s) (e.g. LTC$_4$ synthase, or modification thereof and/or a nucleic acid capable of encoding them) and optionally includes a pharmaceutically-acceptable and compatible carrier(s).

It is contemplated that pharmaceutical compositions comprising nucleic acids that are capable of encoding full-length LTC$_4$ synthase or modification thereof could be used in gene therapy procedures.

The term "pharmaceutically-acceptable and compatible carrier" as used herein, and described more fully below, refers to (i) one or more compatible solid or liquid filler diluents or encapsulating substances that are suitable for administration to a human or other animal, and/or (ii) a system, such as a retroviral vector, capable of delivering a nucleic acid to a target cell.

In the present invention, the term "carrier" thus denotes an organic or inorganic ingredient, natural or synthetic, with which the active ingredient is combined to facilitate application. The term "therapeutically-effective amount" is that amount of the present pharmaceutical composition that produces a desired result or exerts a desired influence. In particular, a "therapeutically-effective" amount of the pharmaceutical compositions of the present invention is an amount that detectably inhibits or enhances activity of LTC$_4$ synthase in vivo or in vitro. Those of ordinary skill in the art will recognize that modulators of human LTC$_4$ synthase may have potential therapeutic applications. Any LTC$_4$ synthase assay may be used to detect inhibition or enhancement of LTC$_4$ synthase, including those LTC$_4$ assays described herein (see Example 1).

The term "compatible", as used herein, means that the components of the pharmaceutical compositions are capable of being commingled with the nucleic acid and/or polypeptides of the present invention, and with each other, in a manner such that there is no interaction that would substantially impair the desired pharmaceutical efficacy.

The molecules of the invention may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group.

The pharmaceutical compositions of the invention include those suitable for oral, rectal, topical, nasal, ophthalmic or parenteral administration, all of which may be used as routes of administration using the materials of the present invention. Other suitable routes of admiration include intrathecal administration directly into spinal fluid (CSF), direct injection onto an arterial surface and intraparenchymal injection directly into targeted areas of an organ. The term "parenteral" includes subcutaneous injections, intravenous, intramuscular, intrasternal injection or infusion techniques.

Pharmaceutical compositions of the present invention may be in a form suitable for oral administration. For example, pharmaceutical compositions of the invention may be presented as capsules, cachets, tablets, troches, lozenges, aqueous or oily suspensions, dispersible powders or granules, emulsions, hard or soft capsules, or syrups or elixirs. Capsules, cachets, tablets, and lozenges may contain the active ingredient in liposomes or as a suspension in an aqueous liquor or non-aqueous liquid such as a syrup, an elixir, or an emulsion.

Aqueous suspensions may contain the active materials in admixture with excipients suitable for the manufacture of aqueous suspensions. Such excipients may be (1) suspending agents such as sodium carboxymethoylcellulose, methylcellulose, hydroxypropylmethylcellulose, sodium alginate, polyvinylpyrrolidone, gum tragacanth and gum acacia; (2) dispersing or wetting agents which may be (a) a naturally-occurring phosphatide such as lecithin, (b) a condensation product of an alykylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

The pharmaceutical compositions of the invention may also be in the form of oil-in-water emulsions. The oily phase may be a vegetable oil such as olive oil or arachis oils, or mineral oil such as liquid paraffin or mixture thereof.

Suitable emulsifying agents may be (1) naturally-occurring gums such as gum acacia and gum tragacanth, (2) naturally-occurring phosphatides such as soy bean and lechithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic monoor diglycerides. In addition, fatty acids such as oleic acid find use in the preparation of injectibles.

The pharmaceutical compositions of the invention may include a sustained release delivery system. Preferred sustained release delivery systems are those that can provide for release of the active compounds in sustained release pellets or capsules. Many types of sustained release delivery systems are available (see, for example, U.S. Pat. No. 5,252,318). These include, but are not limited to, (i) erosional systems in which the active compounds are contained within a matrix (see, for example, U.S. Pat. Nos. 4,452,775; 4,667,014; 4,748,024; and 5,239,660; and (ii) diffusional systems in which the active compounds permeate at a controlled rate through a polymer (see, for example, U.S. Pat. Nos. 3,832,252; and 3,854,480).

Alternatively, the pharmaceutical compositions of the invention may include a delivery system such as, for example, a liposome delivery system. Liposomes are single- or multi-compartmented bodies obtained when lipids are dispersed in aqueous dispension. The walls of the compartments are membranes that are composed of a continuous lipid bi-layer that encloses an inner space. Liposomes can be used, for example, to encapsulate and deliver pharmaceutical agents.

The invention will be further illustrated by the following, non-limiting examples:

EXAMPLE 1

Cloning and Sequencing the Human $LTC_4$ Synthase Gene

Materials and Methods $LTC_2$ (see Nicholson et al., Eur. J. Biochem., 209: 725-FIG. 6B) and $LTA_4$-methyl ester were synthesized by Dr. Bernd Spur while he was at Harvard University. MK-886, mouse monoclonal $LTC_4$ antibodies and a FLAP cDNA probe (A. Ford-Hutchinson, Merck Frosst) and A79175 (G. Carter, Abbott Laboratories) were generous gifts. Total RNA from human eosinophils developed in vitro from human umbilical cord blood mononuclear leukocytes cultured for 28 days with human recombinant interleukin 3 and interleukin 5 was provided by Joshua Boyce (Harvard Medical School). $LTA_4$ was hydrolyzed as described by Maycock et al., J. Biol. Chem. 257: 13911–13914 (1982). $LTC_2$-LC-Biotin was synthesized by coupling $LTC_2$ with NHS-LC-Biotin (1:10 ratio) at pH 7.4 in Tris-HCl buffer at room temperature for 120 min with a conjugation rate of over 95%. The mixture was purified by high performance liquid chromatography (HPLC) with an isocratic solvent system containing 24.9% $H_2O$, 1% acetic acid, 75% methanol, pH 5.0.

KG-1 cells and Raji cells (American Type Culture Collection) were cultured in RPMI-1640 supplemented with 10% fetal calf serum and 15 µg/ml gentamicin under a humidified atmosphere of 95% $O_2$/5% $CO_2$ at 37° C. COS-7 cells were cultured in RPMI-1640 supplemented with 10% heat-inactivated fetal calf serum and 15 µg/ml gentamycin under identical culture conditions. Human PMN and eosinophils were obtained from normal volunteers and isolated as described by Weller et al., Proc. Nat. Acad. Sci. USA, 80: 7626–7630 (1983).

mRNA Isolation and pcDNA3 Library Construction

Messenger RNA (mRNA) was prepared from $2 \times 10^8$ KG-1 cells with a FastTrack mRNA (InVitrogen, San Diego, Calif.) isolation kit according to the manufacturer's instructions. A plasmid cDNA library (pcDNA) was constructed from the mRNA by InVitrogen briefly as follows: The first strand cDNA was synthesized from mRNA using Not oligo T priming. cDNAs were sized by agarose gel electrophoresis, and those greater than 500 base pairs (bp) were ligated with a EcoRI/BstXI adaptor and cloned into the pcDNA3 mammalian expression vector (obtained from InVitrogen, San Diego, Calif.). The pcDNA3 library was used to transform E. coli strain Top $10F^1$ with a complexity of 1.76 million original clones.

Development of cDNA Library

Exactly 96 pools of 2500 E. coli strain Top $10F^1$ colonies each were aliquoted from the KG-1 pcDNA3 library and grown in 100 µl SB medium (containing 5 g/l NaCl, 32 g/l tryptone, 20 g/l yeast extract, and 50 mg/l ampicillin) in a 96-well flat-bottom microtiter plate at 37° C. overnight to amplify each pool. Then, 20-µl samples of bacterial culture from each well were transferred separately into a 10-ml conical tube containing 3 ml of SB medium, and the remaining 80 µl were frozen at −20° C. in 15% glycerol for later rounds of screening. Bacterial cultures in the conical tubes were grown at 37° C. for 18 h, and a 1.5-ml sample of each was subjected to alkaline hydrolysis to develop miniature preparations of plasmids. See, Freeman et al., J. Immunol., 143: 2714–2722 (1989), incorporated herein by reference. Plasmids were dissolved in 25 µl of Tris-EDTA buffer and a 5-µl sample of each was used for COS cell transfection.

Transfection and Screening

COS-7 cells were transfected with plasmid DNA from the KG-1 pcDNA3 library using a DEAE-dextran technique as described by Seed and Aruffo, Proc. Nat. Acad. Sci. USA, 84: 3365–3369 (1987). Briefly, COS-7 cells at about 50% confluence are transfected in 1.5 ml of Dulbecco's or Iscove's modified Eagle's medium (DMEM or IMDM) with 10% NuSerum (Collaborative Research, Waltham, Mass.); 400 micrograms DEAE-dextran per ml; 100 micromolar chloroquine diphosphate; and miniprep plasmid DNA.

Seventy-two hours after transfection, the COS cells were harvested by trypsinization. Twenty thousand cells from each plate were resuspended in 500 µl of culture medium and incubated with 25 µM $LTA_4$ substrate for 30 min on ice to allow the synthesis of intracellular leukotriene product ($LTC_4$). Cells were washed and resuspended in 37° C. medium containing 20 mM serine-borate for 10 min to release intracellular $LTC_4$ into the medium. Cells were pelleted, and the $LTC_4$ in the supernatants was measured by immunoassay.

A positive pool was defined as having produced an amount of $LTC_4$ that was 2 standard deviations above the mean value for all plates in that particular transfection experiment. Any pools that met the definition for positive were simultaneously rescreened in duplicate, and the amounts of $LTC_4$ produced were compared to the mean of 10 controls that were transfected with irrelevant plasmid DNA (CD40 plasmid DNA). A positive pool at this stage was defined as producing an amount of $LTC_4$ that was 5 standard deviations above the mean of the control transfectants.

Once a positive pool was identified, its frozen stock from the 96-well microtiter plate was thawed, titered, and subdivided into smaller pools of about 50 colonies each; these pools were distributed to SB-agar plates containing 50 μg/ml ampicillin. After overnight growth, each plate was replicated by overlaying a nitrocellulose membrane and transferring the membrane to an empty plate. Each membrane was then submerged in 10 ml of SB medium and subjected to intermittent agitation for 10 min by pipeting SB medium to elute the bacterial colonies from the nitrocellulose membranes. The replicate eluted colonies were grown at 37° C. overnight for plasmid preparation. The original plates were cultured at 37° C. for an additional 6 h to replenish the bacterial colonies and were held at 4° C. until a final screening by plasmid preparations of individual colonies of a positive plate.

For these later rounds of screening, samples of transfected COS cells ($5\times10^5$ cells each) were incubated with 20 μM $LTA_4$-methyl ester (ME) substrate for 10 min at 37° C. in the presence of 20 mM serine-borate. Reactions were terminated by the addition of 3 volumes of methanol containing prostaglandin $B_2$ ($PGB_2$). Total $LTC_4$-ME was quantitated by reverse phase-high performance liquid chromatography (RP-HPLC) to confirm the identity of the product by retention time and UV spectra. $LTA_4$-ME was used as substrate instead of the free acid because it provides a high $V_{max}$ (Yoshimoto et al., J. Clin. Invest., 81: 866–871 (1988) and because we had devised an automated HPLC system to detect and quantitate $LTC_4$-ME every 18 min. This assay had the additional advantage of confirming that the product released by transfected COS cells after incubation with $LTA_4$-ME was $LTC_4$-ME based upon its retention time and the on-line UV spectra.

DNA Sequencing

Plasmids were prepared with a Nucleobond isolation kit (Nest) and were sequenced as described by Sanger et al., Proc. Nat. Acad. Sci. USA, 74: 5463–5467 (1977) using dye-labeled dideoxy nucleotides as terminators. Samples were analyzed on an Applied Biosystems model 373A automated DNA sequencer at the Molecular Biology Core Facility, Dana Farber Cancer Institute. See also, Smith et al., Nature 321: 674–679 (1986). Double strand sequencing was performed on one clone producing $LTC_4$ activity (clone 56-12-8), whereas the other two clones producing LT $C_4$ activity (clones 56-13-25 and 56-16-3) were sequenced on the sense strand only.

Reverse Phase-HPLC

HPLC was carried out with a model 126 dual pump system and model 167 scanning UV detector (Beckman Instruments) controlled by an IBM PS2/50 computer using Beckman System Gold software. Samples were applied to a 5-μm 4.6×250-mm C18 Ultrasphere reverse phase column (Beckman Instruments) equilibrated with a solvent of methanol/acetonitrile/water/acetic acid (10:15:100:0.2, v/v), pH 6.0 (solvent A). After injection of the sample, the column was eluted at a flow rate of 1 ml/min with a programmed concave gradient (System Gold curve 6) to 30% solvent A and 70% pure methanol (solvent B) over 0.2 min. After 2.8 min more, solvent B was increased linearly to 90% over 2 min and was maintained at this level for an additional 10 min. UV absorbance at 280 nm and the UV spectra were recorded simultaneously. The retention times for $PGB_2$ and $LTC_4$-ME were 8.5 and 10.1 min, respectively. $LTC_4$-ME was quantitated by calculating the ratio of the peak area to the area of the internal standard $PGB_2$.

Native and Recombinant Protein Purification and Sequencing

Subcellular localization of $LTC_4$ synthase followed the procedure of Penrose et al., Proc. Nat. Acad. Sci., USA, 89: 11603–11606 (1992), incorporated herein by reference. Briefly, native KG-1 or COS-7 cells were harvested by centrifugation at 1000×g for 10 min at 4° C. and washed in a small amount of buffer A (50 mM HEPES/5 mM 2-mercaptoethanol/1 mM EDTA (ph 7.6)). The cells were suspended in buffer containing 50 mM HEPES, 0.25 M sucrose, 5 mM 2-mercaptoethanol, 1 mM EDTA and 10% glycerol (pH 7.6) and sonicated on ice. The sonicate was centrifuged and 1000×g for 10 min to sediment cell debris. The supernatant was centrifuged at 10,000×g for 10 min, decanted to new centrifuge tubes, and spun at 100,000×g to obtain pellets containing microsomes and supernatants containing cytosol. Microsomal and cytosolic fractions were then assayed for $LTC_4$ synthase activity (see immunoassay described herein) to determine subcellular localization of $LTC_4$ synthase (i.e., microsome vs. cytosol).

Detergent-solubilize $LTC_4$ synthase from $6\times10^{10}$ native KG-1 cells (using 0.4% deoxycholate, 0.4% Triton X-102, 10% glycerol) was purified by S-hexylglutathione-agarose chromatography using procedures adapted from Penrose et al., Proc. Nat. Acad. Sci., USA, 89:, above, followed by $LTC_2$ affinity chromatography. Active fractions purified from the S-hexylglutathione-agarose column were combined, concentrated (Amicon, Danvers, Mass.) and then loaded onto an $LTC_2$ affinity column equilibrated with buffer A and 0.1% Triton X-102. The column was washed with the same buffer and the enzyme was eluted with buffer A, containing 0.1% Triton X-102, 0.5 M NaCl and 5 mM reduced glutathione.

The $LTC_4$ synthase activity contained a single 18-kDa protein by sodium dodecyl sulfate-polyacrylamide gel electrophoresis ($NaDodSO_4$-PAGE) with silver staining. This fraction did not conjugate GSH to 1-chloro-2,4-dintrobenzene. A sample of the purified protein was concentrated and added to an equal volume of reducing buffer, and the mixture was boiled for 5 min. The reduced protein in this solution was bound to a polyvinylidene membrane by incubation overnight at 4° C. The bound protein was analyzed for N-terminal amino acid sequence by automated Edman degradation or was digested in situ with trypsin. Fernandez et al., Anal. Biochem., 201: 255–264 (1992). The resulting peptide mixture was separated by narrow-bore HPLC, and a prominent peptide was sequenced by automated Edman degradation on an Applied Biosystems 477A protein sequencer at the Harvard Microchemistry Department. See also, Lane et al., J. Prot. Chem., 10: 151–160 (1991).

$LTC_4$ synthase was purified from COS-7 cell transfectants by the identical sequential S-hexylglutathione and $LTC_2$ affinity chromatography procedures described above.

Northern Blot Analysis

Total RNA (10 micrograms) from human eosinophils were developed in vitro were electrophoresed in formaldehyde/agarose gels, transblotted onto Zetabind and probed under conditions of high stringency (wash temperature 65° C.) with an $LTC_4$ synthase cDNA probe (nucleotides 1–520 of SEQ ID NO.: 1). The probe was produced by digesting 10 micrograms of SEQ ED NO.: 1 with 10 units each of EcoRI and SMAI at 37° C. overnight and separated on 1 percent agarose gel. The RNA blot was then striped and probed with cDNA derived from FLAP.

Autoradiography exposure was 24 hours at −80° C. with two enhancing screens.

Functioning of $LTC_4$ Synthase in COS Cells: Fluorescence-linked Competitive Immunoassay for $LTC_4$ This is a novel assay based, in part, on the discovery of a distinct $LTC_4$ cell transport step following biosynthesis. Release of $LTC_4$ from human eosinophils is time dependent at 37° C. but release of $LTC_4$ formed at this temperature, or even at 0° C., is fully inhibited at zero degrees, resulting in the intracellular retention of accumulated $LTC_4$. Thus, cells can be preloaded with $LTC_4$ at low temperatures. See Lam et al., J. Biol. Chem., 264: 12885–12889 (1989), incorporated herein by reference.

COS cells possess a low basal capability to conjugate glutathione to $LTA_4$, perhaps due to a cytosolic glutathione S-transferase. Therefore, screening for enzymatic activity in transfected cells requires an assay that is sensitive enough to distinguish the incremental production of $LTC_4$ by a single clone within a pool. We developed a competitive fluorescence-linked immunoassay for $LTC_4$, with exquisite sensitivity and the high volume efficiency necessary for expression cloning of the $LTC_4$ synthase. In addition, the signal to background ratio for the production and release of $LTC_4$ from transfected cells was optimized by providing substrate $LTA_4$ at 4° C. This step allowed $LTA_4$ uptake and $LTC_4$ biosynthesis without release until the cells had been washed and warmed. The transfected COS-7 cells exhibited the same temperature-dependent $LTC_4$ export step(s) previously observed. See Lam et al., J. Biol. Chem., id. Because of the wash step and the assay sensitivity, a signal to noise ratio was achieved that proved suitable for assaying all pools at the same cell number to minimize the plate-to-plate variation in cell numbers of transfected COS cells per plate.

Leukotriene $C_4$ synthase was generated from COS-7 cells transfected with cDNA from a KG-1 pcDNA mammalian KG-1 expression library, as described above. Cells were held at 4° C. to ensure intracellular retention of $LTC_4$ generated during the incubation with substrate. The temperature was then raised to 37° C. to allow for the export of $LTC_4$ into the incubation medium.

KG-1 cells were harvested by centrifugation and resuspended in Hanks' balanced salt solution (HBSS) at $10^7$ cells/ml. After warming to 37° C., NHS-LC-Biotin was added to achieve a final concentration of 350 μg/ml, and the mixture was incubated for 30 min to biotinylate the KG-1 cell membranes. The biotinylated cells were washed twice with HBSS containing 2 mg/ml bovine serum albumin (HBSA) to remove excess and un-reacted biotin and were incubated with 2 mg/ml avidin in HBSA. After 30 min, the biotin-avidin-coupled KG-1 cells were washed twice to remove excess avidin and were incubated with 600 ng/ml $LTC_2$-LC-Biotin for 30 min at 37° C. to link the $LTC_2$-biotin complex onto the cell surface via the previously bound avidin.

After washing the KG-1 cells, samples of $10^5$ cells each were then incubated either with (i) 0–200 pg of synthetic $LTC_4$ or (ii) with 5–10 μl portions of the warmed incubation medium from transfected COS cells. The incubation medium contained unknown amounts of released $LTC_4$. After incubation for 3 min, mouse monoclonal anti-$LTC_4$ antibodies were added (final dilution 1:10,000), and the KG-1 cells were incubated for 30 min at room temperature, washed, and incubated with fluorescein isothiocyanate-conjugated goat anti-mouse Fab[1] antiserum (1:30 dilution) for 40 min on ice in the dark. The cells were washed, resuspended in 1 ml of HBSA containing 1 mM EDTA, and analyzed by flow cytometry for cell surface fluorescence intensities.

This immunoassay measures the competition between released $LTC_4$ in solution and membrane bound $LTC_2$ for anti-$LTC_4$ as analysed by decrements in binding of fluorescence-linked secondary antibody. Thus, the more $LTC_4$ that is in solution, the less antibody that will be available for binding to the $LTC_2$ on the cell surface. The immunoassay is capable of detecting as little as 2.5 pg of $LTC_4$ with a linear dose response between 10 and 100 pg of $LTC_4$.

It will be appreciated by those having ordinary skill in the art that inert materials may be substituted for KG-1 cells in this assay. That is, an inert carrier such as, for example, agarose beads may be coupled to avidin and used in the method, provided that the beads are of sufficient size to be assayed with flow cytometry. The assay described herein may be used to detect and quantify any product that can be biotinylated and linked to a carrier.

Dose-Response Assay using MK886

Cell lysates of the COS-7 cell transfectant containing SEQ ID NO.: 1 were incubated with 20 micromolar $LTA_4$-ME, 20 mM GSH, 5 mM $MgCl_2$ in HEPES buffer (pH 7.6), in the presence of 0–10 micromolar MK-886 for 10 minutes at room temperature. Reactions were stopped by addition of 2 volumes of methanol containing 200 ng PGB2. Samples were analyzed by RP-HPLC.

RESULTS

Expression Cloning

Of the plasmids from the 96 pools (2500 colonies each) of the KG-1 pcDNA3 library transfected into COS-7 cells, only a single pool produced an $LTC_4$ value (207 pg/$10^4$ cells) that was 5 standard deviations above the mean (64.2±8 pg/$10^4$ cells).

This pool was divided into smaller pools of about 50 colonies each, colonies plated on SB-agar, and subjected to a second round of screening with $LTA_4$-ME as substrate. Three highly positive plates, numbers 56-12 (4,988 pg/$10^4$ cells), 56-13 (3,419 pb/$10^4$ cells), and 56-16 (3,850 pg/$10^4$ cells), were identified. COS-7 cells transfected with plasmid from other plates did not make detectable amounts of $LTC_4$-ME.

When individual colonies from each plate were grown and their plasmids prepared and transfected into COS-7 cells, only one colony producing $LTC_4$ synthase activity was identified from each plate, namely, clones 56-12-8 (7,485 pg/$10^4$ cells), 56-13-25 (6,391 pg/$10^4$ cells), and 56-16-3 (7,583 pg/$10^4$ cells).

Nucleotide Sequence of cDNA

Clone 56-12-8 contained a 694-bp insert with an open reading frame of 450 bp terminated by a TGA stop codon (SEQ ID NO.: 1). The nucleotide sequence was identical for the two other clones, 56-13-25 and 56-16-3, producing $LTC_4$ synthase activity at high levels.

Consensus Amino Acid Sequence of $LTC_4$ Synthase and RNA Blot Analysis

The $LTC_4$ synthase protein obtained by sequential S-hexyl glutathione and $LTC_2$ affinity chromatography of solubilized $LTC_4$ from native KG-1 cells provided a 22 amino acid N-terminal sequence of MKDEVAL-LAAVTLLGVLLQAYF (SEQ ID NO. 9) that corresponds exactly to the N-terminal amino acid sequence (SEQ ID NO.: 2) deduced from the cDNA of SEQ ID NO.: 1. An internal peptide fragment of the protein provided a sequence of VSPPLTTGPPEFER (SEQ ID NO. 3) in which all 14 amino acid residues are identical to the deduced amino acid sequence amino acid residues 35–48 of SEQ ID NO.: 2.

RNA isolated from human eosinophils developed in vitro demonstrated a 0.7-kilobase pair mRNA transcript (data not shown). The FLAP transcript in these same cells was approximately 1.0 kilobase. The 0.7-kilobase $LTC_4$ synthase mRNA transcript was also detected in total RNA from the KG-1 cells and less abundantly in peripheral blood eosinophils. No transcript was detected in human PMNs and Burkitt's lymphoma Raji cell line, which lack $LTC_4$ synthase function. When compared with FLAP mRNA transcript by autoradiography, $LTC_4$ synthase transcript is less intense than those of FLAP. The FLAP transcript in these same cells was approximately 1.0 kilobase. The 0.7-kilobase $LTC_4$ synthase mRNA transcript was also detected in total RNA from the KG-1 cells and less abundantly in peripheral blood eosinophils. No transcript was detected in human PMNs and Burkitt's lymphoma Raji cell line, which lack $LTC_4$ synthase function. When compared with FLAP mRNA transcript by autoradiography, $LTC_4$ synthase transcript is less intense than those of FLAP.

Microsomal Localization, Size and Inhibition of Function of the Protein Expressed in COS Cells.

When examined for subcellular localization, 87–89% (n=3) of the activity of the recombinant protein was in the microsomal fraction.

$LTC_4$ synthase purified from COS cell transfectants by sequential S-hexyl-GSH and $LTC_2$ affinity chromatography migrated as an 18-kDa protein by $NaDodSO_4$-PAGE, identical in size to the native enzyme purified from KG-1 cells (data not shown).

Lysates from transfected COS cells were analysed for $LTC_4$, the product of conjugating reduced glutathione with 5,6-oxido-7,9-E-11,14-Z-eicosatetraenoic acid. MK-886, a FLAP inhibitor (see Dixon et al., Nature 343: 6255 (1990) and Gillard et al., Can. J. Physil ol. Pharmac., 67: 456 (1989), both of which incorporated herein by reference), dose-dependently inhibited the conversion of 20 uM $LTA_4$-ME to $LTC_4$-ME by COS cell lysates with an $IC_{50}$ of less than 3 $\mu M$ (data not shown). At 10 $\mu M$, MK-886 inhibits more than 90% of the enzyme activity. In contrast, a 5-lipoxygenase inhibitor, A79175, did not affect $LTC_4$ synthase activity in COS cell lysates at a concentration of 10 $\mu M$.

EXAMPLE 2

Isolating a Homolog of $LTC_4$ Synthase

A portion of the human leukotriene $C_4$ synthase gene is amplified from human eosinophil DNA using the polymerase chain reaction technique (Saiki, R. K., et al., 1985, Science 230 1350–1354) using NotI-SalI sites in the PCR primers. The 100 $\mu l$ reaction contains 10 mM Tris-HCl pH 8.3, 50 mM KCl, 0.001% (w/v) Gelatin, 2 mM $MgCl2$, 200 $\mu M$ dNTPs, 1.5 $\mu M$ SEQ ID NO.: 1, 1.5 $\mu M$ primer sequence (e.g., SEQ ID NOS. 4 and 5), 2.5 units Taq Polymerase (Perkin Elmer Cetus), and 1.0 $\mu g$ of human eosinophil DNA. The DNA Thermal-cycler (Perkin Elmer Cetus, Model N801) is programmed for the following incubations:

1. 94° C., 2 min. (initial denaturation)
2. 94° C., 1 min. (denaturation)
3. 50° C., 1 min. (annealing)
4. 72° C., 3 min. (elongation)
5. Steps 2–4 cycle 50 times (amplification)
6. 4° C., Soak (storage)

The DNA amplified in this reaction is electrophoresed on 5% polyacrylamide gels to verify band length. If the size is determined to be correct, the DNA is purified by phenol extraction, then digested with NotI and SalI to remove the termini. The DNA is then ligated into the NotI/SalI site of vector pUC19 (New England Biolabs). The DNA is transformed into E. coli strain DH5-alpha made competent by the $CaCl_2$ procedure (Hanahan, D., 1983, J. Mol. Biol. 155:557). The human leukotriene $C_4$ synthase is then sequenced by the chain-termination method (Sanger, F. et al., 1977, Proc. Natl. Acad. Sci. USA 74:5463).

An alternate cloning procedure for genomic DNA or cDNA encoding human leukotriene $C_4$ synthase includes generating oligonucleotides from the polymerase chain reactions described above and radioactively labeling them according to the procedure described in Sambrook et al. (1989). These oligonucleotides are used to screen a $\lambda$gt11 genomic library from a human cell line. Alternatively, a $\lambda$gt11 cDNA library prepared from mRNA from the same human cell line is used. Construction of these libraries follows the procedure of Sambrook, J. et al., Molecular Cloning, (1989). Alternatively, a commercially available library, available from Clontech (Palo Alto, Calif.), is used.

Hybridization conditions are as described by Cate et al., Cell, 45:165 (1986), except that the final wash in tetramethyl ammonium chloride is omitted. DNA inserts from positive plaques are subcloned directly into the plasmid vector pBluescript SKM13+ (Stratagene, Inc. San Diego, Calif.). Positive plasmid subclones are identified by colony hybridization, with the use of the same oligonucleotide hybridization probe. Minipreparations of plasmid DNA are prepared from positive colonies.

The nucleotide sequence immediately upstream from the oligonucleotide binding site is determined by double stand sequencing (Chen and Seeburg, DNA, 4:165 1985), using $^{32}P$ end-labeled oligonucleotide as sequencing primer and non-radioactive nucleotides in the extension reactions. Subclones whose codon order upstream from the priming site match the known human amino acid sequence (SEQ. ID. NO. 2) are sequenced in their entirety by the diideoxy chain termination method, with either the Klenow fragment of Escherichia coli DNA polymerase I or modified bacteriophage T7 DNA polymerase (Sequenase; United States Biochemicals) in the extension reactions. Subclones are sequenced from their termini, from both directions from a set of restriction sites. Clones are obtained whose codon order is at least partially similar to the amino acid sequence of human leukotriene $C_4$ synthase polypeptide. A full-length genomic or cDNA sequence for human leukotriene $C_4$ synthase polypeptide is assembled from overlapping partial clones.

EXAMPLE 3

Expression of Polypeptide

The following method for transient expression of leukotriene $C_4$ synthase cDNA in cultured cells is adapted from Birnir et al., supra.

COS-7 cells, or other cultured cells are used. Tissue culture medium, serum, and antibiotics are obtained from GIBCO (Gaithersburg, Md.).

The eukaryotic expression vector pEUK-C1 is obtained from Clontech (Palo Alto, Calif.). Plasmid pEUK-UT2 is constructed by inserting SEQ ID NO.: 1 cDNA (blunt-ended with T4 DNA polymerase) into the SmaI side of plasmid pEUK-C1. The orientation and correct insertion at the 5' end is confirmed by DNA sequencing. pEUK-UT2 (15 $\mu g$) is transfected into COS-7 cells using lipofectin. Briefly, COS-7 cells are seeded onto 35 mm tissue culture plates (Falcon, N.J.) in Dulbecco's modified Eagle's medium (DMEM) with 10% fetal bovine serum and 1% antimycotic (containing Fungizon-GIBCO) and transfected at a confluency of 80–95%. Immediately before transfection, cell monolayers are washed twice with OPTI-MEM I medium (GIBCO). For each 35 mm plate, 15 μg of plasmid and 15 μg of Lipofectin are mixed for 30 min in 0.5 ml of OPTI-MEM I medium and then added to the plate.

After incubation for 24 h at 37° C. in a humidified atmosphere containing 5% $CO_2$, 1 ml of DMEM with 10% serum is added. $LTC_4$ synthase is measured 48 to 72 h post-transfection.

In control experiments, pEUK-C1 plasmid DNA without SEQ ID NO.: 1 is transfected. The transfection efficiency is monitored after co-transfection with plasmid pCH110 (Clontech), containing a functional Lac Z gene and a SV 40 origin of replication. COS-7 cells produce the SV 40 large tumor antigen which allows replication of plasmids (such as pCH110 and pEUK-C1) containing a SV 40 origin. The product of the Lac Z gene, beta-galactosidase, is measured using X-Gal. Generally, between 15–25% of cells are transfected.

EXAMPLE 4

Preparation of Constructions for Transfections and Microinjections

Methods for purification of DNA for microinjection are well known to those of ordinary skill in the art. See, for example, Hogan et al., *Manipulating the Mouse Embryo*, Cold spring Harbor Laboratory, Cold Spring Harbor, N.Y. (1986); and Palmer et al., *Nature*, 300: 611 (1982).

Construction of Transgenic Animals

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA*, 82: 4438–4442 (1985)). Embryos can be infected with viruses, especially retroviruses, modified to bear human leukotriene $C_4$ synthase genes of the invention.

Pluripotent stem cells derived from the inner cell mass of the embryo and stabilized in culture can be manipulated in culture to incorporate human leukotriene $C_4$ synthase genes of the invention. A transgenic animal can be produced from such cells through implantation into a blastocyst that is implanted into a foster mother and allowed to come to term.

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. $B6D2F_1$ males can be used for mating and vasectomized Swiss Webster studs can be used to stimulate pseudopregnancy. Vasectomized mice and rats can be obtained from the supplier.

Microinjecion Procedures

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47: 897–905 (1991). Other procedures for introduction of DNA into tissues of animals are described in U.S. Pat. No. 4,945,050 (Sanford et al., Jul. 30, 1990).

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline (DPSS) with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats

The procedure for generating transgenic rats is similar to that of mice See Hammer et al., *Cell*, 63:1099–1112 (1990). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPSS with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of DNA into ES cells:

Methods for the culturing of ES cells and the subsequent production of transgenic animals by the introduction of DNA into ES cells using methods such as electroporation, calcium phosphate/DNA precipitation; and direct injection are well known to those of ordinary skill in the art. See, for example, *Teratocarcinomas and Embryonic Stem Cells, A Practical Approach*, E. J. Robertson, ed., IRL Press (1987). Selection of the desired clone of thrombospondin-4-containing ES cells is accomplished through one of several means. Although embryonic stem cells are currently available for mice only, it is expected that similar methods and procedures as described and cited here will be effective for embryonic stem cells from different species as they become available.

In cases involving random gene integration, a clone containing the human leukotriene $C_4$ synthase gene of the invention is co-transfected with a gene encoding neomycin resistance. Alternatively, the gene encoding neomycin resistance is physically linked to the human leukotriene $C_4$ synthase gene. Transfection is carried out by any one of several methods well known to those of ordinary skill in the art (E. J. Robertson, supra). Calcium phosphate/DNA precipitation, direct injection, and electroporation are the preferred methods. Following DNA introduction, cells are fed with selection medium containing 10% fetal bovine serum in DMEM supplemented with G418 (between 200 and 500 µg/ml biological weight). Colonies of cells resistant to G418 are isolated using cloning rings and expanded. DNA is extracted from drug resistant clones and Southern blotting experiments using a transgene-specific DNA probe are used to identify those clones carrying the human leukotriene $C_4$ synthase polypeptide sequences. In some experiments, PCR methods are used to identify the clones of interest.

DNA molecules introduced into ES cells can also be integrated into the chromosome through the process of homologous recombination. Copecchi, *Science*, 244: 1288–1292 (1989). Direct injection results in a high efficiency of integration. Desired clones are identified through PCR of DNA prepared from pools of injected ES cells. Positive cells within the pools are identified by PCR subsequent to cell cloning. DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Copecchi, supra and Joyner et al., *Nature* 338: 153–156 (1989), the disclosures of which are incorporated herein.

Embryo Recovery and ES Cell Injection:

Naturally cycling or superovulated female mice mated with males are used to harvest embryos for the implantation of ES cells. It is desirable to use the C57BL165 stain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 µm.

Transfer of Embryos to Receptive Females:

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats

Tail samples (1–2 cm) are removed from three week old animals. DNA is prepared and analyzed by Southern blot or PCR to detect transgenic founder ($F_0$) animals and their progeny ($F_1$ and $F_2$). In this way, animals that have become transgenic for the desired human leukotriene $C_4$ synthase genes are identified. Because not every transgenic animal expresses the polypeptide, and not all of those that do will have the expression pattern anticipated by the experimenter, it is necessary to characterize each line of transgenic animals with regard to expression of the leukotriene $C_4$ synthase in different tissues.

Production of Non-Rodent Transgenic Animals

Procedures for the production of non-rodent mammals and other animals have been discussed by others. See Houdebine and Chourrout, supra; Pursel et al., *Science* 244: 1281–1288 (1989); and Simms et al., *Bio/Technology*, 6: 179–183 (1988).

Identification of Other Transgenic Organisms

An organism is identified as a potential transgenic by taking a sample of the organism for DNA extraction and hybridization analysis with a probe complementary to the human leukotriene $C_4$ synthase gene of interest. Alternatively, DNA extracted from the organism can be subjected to PCR analysis using PCR primers complementary to the human leukotriene $C_4$ synthase gene of interest.

EXAMPLE 5

Protocol for Inactivating the Human Leukotriene $C_4$ Synthase Gene

Mouse genomic clones are isolated by screening a genomic library from the D3 strain of mouse with a human leukotriene $C_4$ synthase probe. Duplicate lifts are hybridized with a radiolabeled probe by established protocols (Sambrook, J. et al., *The Cloning Manual*, Cold Spring Harbor Press, N.Y.). Plaques that correspond to positive signal on both lifts are isolated and purified by successive screening rounds at decreasing plaque density. The validity of the isolated clones is confirmed by nucleotide sequencing.

The genomic clones are used to prepare a gene targeting vector for the deletion of human leukotriene $C_4$ synthase polypeptide in embryonic stem cells by homologous recombination. A neomycin resistance gene (neo) with its transcriptional and translational signals, is cloned into convenient sites that are near the 5' end of the gene. This will disrupt the coding sequence of human leukotriene $C_4$ synthase polypeptide and allow for selection by the drug Geneticin (G418) by embryonic stem (ES) cells transfected with the vector. The Herpes simplex virus thymidine kinase (HSV-tk) gene is placed at the other end of the genomic DNA as a second selectable marker. Only stem cells with the neo gene will grow in the presence of this drug.

Random integration of this construct into the ES genome will occur via sequences at the ends of the construct. In these cell lines, the HSV-tk gene will be functional and the drug gancyclovir will therefore be cytotoxic to cells having an integrated sequence of the mutated human leukotriene $C_4$ synthase coding sequence.

Homologous recombination will also take place between homologous DNA sequences of the ES human leukotriene $C_4$ synthase genome and the targeting vector. This usually results in the excision of the HSV-tk gene because it is not homologous with the human leukotriene $C_4$ synthase gene.

Thus, by growing the transfected ES cells in G418 and gancyclovir, the cell lines in which homologous recombination has occurred win be highly enriched. These cells will contain a disrupted coding sequence of human leukotriene $C_4$ synthase. Individual clones are isolated and grown up to produce enough cells for frozen stocks and for preparation of DNA. Clones in which the human leukotriene $C_4$ synthase gene has been successfully targeted are identified by Southern blot analysis. The final phase of the procedure is to inject targeted ES cells into blastocysts and to transfer the blastocysts into pseudopregnant females. The resulting chimeric animals are bred and the offspring are analyzed by Southern blotting to identify individuals that carry the mutated form of the gene in the germ line. These animals will be mated to determine the effect of human leukotriene $C_4$ synthase polypeptide deficiency on murine development and physiology.

DISCUSSION $LTC_4$ synthase, an integral membrane protein that conjugates reduced glutathione (GSH) to $LTA_4$ but not to xenobiotics, provides the parent $LTC_4$ for the cysteinyl leukotriene family, and is the only biosynthetic moiety in the 5-lipoxygenase pathway that has not yet been defined by its cDNA, protein structure, or gene family. Recently, a 35-amino-acid N-terminal sequence was obtained for $LTC_4$ synthase extracted and purified from the THP-1 cell line. Nicholson et al., Proc. Nat. Acad. Sci., USA 90: 2015–2019 (1993). The amino acid N-terminal sequence obtained for the KG-1 cell line described herein (SEQ ID NO.: 9) differed from that of the THP-1 cell line only at position 21; an internal 14 residue peptide (SEQ ID NO.: 3) provided an additional amino acid sequence that corresponded to residues 35 to 48 of LT $C_4$ from KG-1 cells.

Nonetheless, the degeneracy of the nucleotides coding for the observed THP-1 sequence data is extremely high and did not provide oligonucleotide probes capable of hybridizing to clones carrying the sequence of interest using a λgt11 KG-1 cDNA library (unpublished data). We thus proceeded to expression cloning with the intent of using the available THP-1 protein sequence at the N-terminal amino acid residues for reference, but depending on enzymatic function for detection and definition of the cDNA and its amino acid sequence.

We have also demonstrated that FLAP inhibitor, MK-886, inhibits $LTC_4$ synthase activity from transfected COS cell lysates in a dose-related fashion with an $ID_{50}$ of about 3 $\mu$M. Since FLAP binds arachidonic acid for presentation to 5-lipoxygenase that is engaged in calcium-dependent membrane association (Mancini et al., FEBS Lett., 318: 277–281 (1993) for synthesis of $LTA_4$, it seems plausible that the transmembrane domains of $LTC_4$ synthase homologous to FLAP will accept $LTA_4$ for conjugation with glutathione at/or in the membrane.

$LTA_4$ and reduced glutathione conjugate spontaneously in a basic microenvironment. See Radmark et al., J. Biol. Chem., 12339–12345 (1984). It may be that the putative binding of $LTA_4$ to $LTC_4$ synthase, a protein with a pI of 11.05, allows a favorable environment for the conjugation with bound or unbound glutathioine with only a modest catalytic boost. Thus, $LTC_4$ synthase may represent a member of the lipid-binding family rather than the classical glutathione S-transferase family. Irrespective of the catalytic mechanisms yet to be elucidated, it is likely that $LTC_4$ synthase represents a member of a novel gene family in which FLAP is also a member.

EQUIVALENTS

It should be understood that the preceding is merely a detailed description of certain preferred embodiments. It therefore should be apparent to those skilled in the art that various modifications and equivalents can be made without departing from the spirit or scope of the invention.

SEQUENCE LISTING

<160> NUMBER OF SEQ ID NOS: 9

<210> SEQ ID NO 1
<211> LENGTH: 622
<212> TYPE: DNA
<213> ORGANISM: Homo sapiens

<400> SEQUENCE: 1

```
agcgttcccc agctcgcctt cacacacagc ccgtgccacc acaccgacgg taccatgaag      60
gacgaggtag ctctactggc tgctgtcacc ctcctgggag tcctgctgca agcctacttc     120
tccctgcagg tgatctcggc gcgcagggcc ttccgcgtgt cgccgccgct caccaccggc     180
ccacccgagt tcgagcgcgt ctaccgagcc caggtgaact gcagcgagta cttcccgctg     240
ttcctcgcca cgctctgggt cgccggcatc ttctttcatg aagggcggc ggccctgtgc     300 ggcctggtct acctgttcgc gcgcctccgc tacttccagg gctacgcgcg ctccgcgcag     360
ctcaggctgg caccgctgta cgcgagcgcg cgcgccctct ggctgctggt ggcgctggct     420
```

```
gcgctcggcc tgctcgccca cttcctcccg gccgcgctgc gcgccgcgct cctcggacgg      480
ctccggacgc tgctgccgtg ggcctgagac caaggccccc gggccgacgg agccgggaaa      540
gaagagccgg agcctccagc tgccccgggg aggggcgctc gcttccgcat cctagtctct      600
atcattaaag ttctagtgac cg                                              622
```

```
<210> SEQ ID NO 2
<211> LENGTH: 147
<212> TYPE: PRT
<213> ORGANISM: Homo sapiens

<400> SEQUENCE: 2
```

| Met | Lys | Asp | Glu | Val | Ala | Leu | Leu | Ala | Ala | Leu | Leu | Gly | Val | Leu | Leu |
|---|---|---|---|---|---|---|---|---|---|---|---|---|---|---|---|
| 1 | | | | 5 | | | | | 10 | | | | | 15 | |

| Gln | Ala | Tyr | Phe | Ser | Leu | Gln | Val | Ile | Ser | Ala | Arg | Arg | Phe | Arg | Val |
|---|---|---|---|---|---|---|---|---|---|---|---|---|---|---|---|
| | | | 20 | | | | | 25 | | | | | 30 | | |

| Ser | Pro | Pro | Leu | Thr | Thr | Gly | Pro | Pro | Glu | Phe | Glu | Arg | Val | Tyr | Arg |
|---|---|---|---|---|---|---|---|---|---|---|---|---|---|---|---|
| | | 35 | | | | | 40 | | | | | 45 | | | |

| Ala | Gln | Val | Asn | Cys | Ser | Glu | Tyr | Phe | Pro | Leu | Phe | Leu | Ala | Thr | Leu |
|---|---|---|---|---|---|---|---|---|---|---|---|---|---|---|---|
| | 50 | | | | | 55 | | | | | 60 | | | | |

| Trp | Val | Ala | Gly | Ile | Phe | Phe | His | Glu | Gly | Ala | Ala | Ala | Leu | Cys | Gly |
|---|---|---|---|---|---|---|---|---|---|---|---|---|---|---|---|
| 65 | | | | | 70 | | | | | 75 | | | | | 80 |

| Leu | Val | Tyr | Leu | Phe | Ala | Arg | Leu | Arg | Tyr | Phe | Gln | Gly | Tyr | Ala | Arg |
|---|---|---|---|---|---|---|---|---|---|---|---|---|---|---|---|
| | | | | 85 | | | | | 90 | | | | | 95 | |

| Ser | Ala | Gln | Leu | Arg | Leu | Ala | Pro | Leu | Tyr | Ala | Ser | Ala | Arg | Ala | Leu |
|---|---|---|---|---|---|---|---|---|---|---|---|---|---|---|---|
| | | | 100 | | | | | 105 | | | | | 110 | | |

| Trp | Leu | Leu | Val | Ala | Leu | Ala | Ala | Leu | Gly | Leu | Leu | Ala | His | Phe | Leu |
|---|---|---|---|---|---|---|---|---|---|---|---|---|---|---|---|
| | | 115 | | | | | 120 | | | | | 125 | | | |

| Pro | Ala | Ala | Leu | Arg | Ala | Ala | Leu | Leu | Gly | Arg | Leu | Arg | Thr | Leu | Leu |
|---|---|---|---|---|---|---|---|---|---|---|---|---|---|---|---|
| | 130 | | | | | 135 | | | | | 140 | | | | |

| Pro | Trp | Ala |
|---|---|---|
| 145 | | |

```
<210> SEQ ID NO 3
<211> LENGTH: 14
<212> TYPE: PRT
<213> ORGANISM: Homo sapiens

<400> SEQUENCE: 3
```

| Val | Ser | Pro | Pro | Leu | Thr | Thr | Gly | Pro | Pro | Glu | Phe | Glu | Arg |
|---|---|---|---|---|---|---|---|---|---|---|---|---|---|
| 1 | | | | 5 | | | | | 10 | | | | |

```
<210> SEQ ID NO 4
<211> LENGTH: 21
<212> TYPE: DNA
<213> ORGANISM: Homo sapiens

<400> SEQUENCE: 4
agcgttcccc agctcgcctt c                                               21

<210> SEQ ID NO 5
<211> LENGTH: 26
<212> TYPE: DNA
<213> ORGANISM: Homo sapiens

<400> SEQUENCE: 5
cggtcactag aactttaatg atagag                                          26

<210> SEQ ID NO 6
```

-continued

```
<211> LENGTH: 24
<212> TYPE: PRT
<213> ORGANISM: Homo sapiens

<400> SEQUENCE: 6

Gln Val Ile Ser Ala Arg Arg Ala Phe Arg Val Ser Pro Pro Leu Thr
 1               5                  10                  15

Thr Gly Pro Pro Glu Phe Glu Arg
            20

<210> SEQ ID NO 7
<211> LENGTH: 24
<212> TYPE: PRT
<213> ORGANISM: Homo sapiens

<400> SEQUENCE: 7

Arg Leu Arg Tyr Phe Gln Gly Tyr Ala Arg Ser Ala Gln Leu Arg Leu
 1               5                  10                  15

Ala Pro Leu Tyr Ala Ser Ala Arg
            20

<210> SEQ ID NO 8
<211> LENGTH: 15
<212> TYPE: PRT
<213> ORGANISM: Homo sapiens

<400> SEQUENCE: 8

Arg Ala Ala Leu Leu Gly Arg Leu Arg Thr Leu Leu Pro Trp Ala
 1               5                  10                  15

<210> SEQ ID NO 9
<211> LENGTH: 22
<212> TYPE: PRT
<213> ORGANISM: Homo sapiens

<400> SEQUENCE: 9

Met Lys Asp Glu Val Ala Leu Leu Ala Ala Val Thr Leu Leu Gly Val
 1               5                  10                  15

Leu Leu Gln Ala Tyr Phe
            20
```

What is claimed is:

1. An antibody, characterized in that, when contacted with an antigenic determinant of a leukotriene $C_4$ synthase, binds specifically to said determinant.

2. The antibody of claim 1, wherein the leukotriene $C_4$ synthase is a mammalian leukotriene $C_4$ synthase.

3. The antibody of claim 1, wherein the leukotriene $C_4$ synthase is a human leukotriene $C_4$ synthase.

4. The antibody of claim 3, wherein the human leukotriene $C_4$ synthase is produced in a cell other than a cell in which the human leukotriene $C_4$ synthase is found in nature.

5. The antibody of claim 4, wherein the human leukotriene $C_4$ synthase comprises an amino acid sequence comprising SEQ ID NO. 2 and is produced in a procaryotic cell.

6. The antibody of claim 5, wherein the procaryotic cell is a bacterial cell.

7. The antibody of claim 4, wherein the human leukotriene $C_4$ synthase comprises an amino acid sequence comprising SEQ ID NO. 2 and is produced in a eukaryotic cell.

8. The antibody of claim 7, wherein the eukaryotic cell is a mammalian cell.

9. The antibody of claim 7, wherein the eukaryotic cell is a monkey cell.

10. The antibody of claim 9, wherein the monkey cell is COS cell.

* * * * *

UNITED STATES PATENT AND TRADEMARK OFFICE
CERTIFICATE OF CORRECTION

PATENT NO. : 6,221,676 B1
DATED : April 24, 2001
INVENTOR(S) : Lam et al.

It is certified that error appears in the above-identified patent and that said Letters Patent is hereby corrected as shown below:

<u>Columns 33 to 38,</u>
Line 23, please delete the existing Sequence Listing and insert the attached therefor.

Signed and Sealed this

Twenty-fifth Day of March, 2003

JAMES E. ROGAN
*Director of the United States Patent and Trademark Office*

SEQUENCE LISTING

<110> Lam, Bing K.
      Penrose, John F.
      Frank, Austen K.

<120> DNA ENCODING HUMAN LEUKOTRIENE C4 SYNTHASE,
      POLYPEPTIDES, AND USES THEREFOR

<130> Docket No. 0092662-0019 (BWH269)

<140> 08/986,837
<141> 1997-12-08

<150> 08/246,991
<151> 1994-05-20

<160> 9

<170> PatentIn Ver. 2.1

<210> 1
<211> 622
<212> DNA
<213> Homo sapiens

<400> 1
agcgttcccc agctcgcctt cacacacagc ccgtgccacc acaccgacgg taccatgaag    60
gacgaggtag ctctactggc tgctgtcacc ctcctgggag tcctgctgca agcctacttc   120
tccctgcagg tgatctcggc gcgcagggcc ttccgcgtgt cgccgccgct caccaccggc   180
ccacccgagt tcgagcgcgt ctaccgagcc caggtgaact gcagcgagta cttcccgctg   240
ttcctcgcca cgctctgggt cgccggcatc ttctttcatg aagggcggc ggccctgtgc   300
ggcctggtct acctgttcgc gcgcctccgc tacttccagg gctacgcgcg ctccgcgcag   360
ctcaggctgg caccgctgta cgcgagcgcg cgcgccctct ggctgctggt ggcgctggct   420
gcgctcggcc tgctcgccca cttcctcccg gccgcgctgc gcgccgcgct cctcggacgg   480
ctccggacgc tgctgccgtg ggcctgagac caaggccccc gggccgacgg agccgggaaa   540
gaagagccgg agcctccagc tgccccgggg aggggcgctc gcttccgcat cctagtctct   600
atcattaaag ttctagtgac cg                                            622

<210> 2
<211> 150
<212> PRT
<213> Homo sapiens

<400> 2
Met Lys Asp Glu Val Ala Leu Leu Ala Ala Val Thr Leu Leu Gly Val
 1               5                  10                  15

1

```
        Leu Leu Gln Ala Tyr Phe Ser Leu Gln Val Ile Ser Ala Arg Arg Ala
                    20                  25                  30

Phe Arg Val Ser Pro Pro Leu Thr Thr Gly Pro Pro Glu Phe Glu Arg
                    35                  40                  45

Val Tyr Arg Ala Gln Val Asn Cys Ser Glu Tyr Phe Pro Leu Phe Leu
                    50                  55                  60

Ala Thr Leu Trp Val Ala Gly Ile Phe Phe His Glu Gly Ala Ala Ala
         65                  70                  75                  80

Leu Cys Gly Leu Val Tyr Leu Phe Ala Arg Leu Arg Tyr Phe Gln Gly
                        85                  90                  95

Tyr Ala Arg Ser Ala Gln Leu Arg Leu Ala Pro Leu Tyr Ala Ser Ala
                    100                 105                 110

Arg Ala Leu Trp Leu Leu Val Ala Leu Ala Ala Leu Gly Leu Leu Ala
                    115                 120                 125

His Phe Leu Pro Ala Ala Leu Arg Ala Ala Leu Leu Gly Arg Leu Arg
                    130                 135                 140

Thr Leu Leu Pro Trp Ala
        145                 150

<210> 3
<211> 14
<212> PRT
<213> Homo sapiens

<400> 3
Val Ser Pro Pro Leu Thr Thr Gly Pro Pro Glu Phe Glu Arg
  1               5                   10

<210> 4
<211> 21
<212> DNA
<213> Homo sapiens

<400> 4
agcgttcccc agctcgcctt c                                               21
```

```
<210> 5
<211> 26
<212> DNA
<213> Homo sapiens

<400> 5
cggtcactag aactttaatg atagag                                    26

<210> 6
<211> 24
<212> PRT
<213> Homo sapiens

<400> 6
Gln Val Ile Ser Ala Arg Arg Ala Phe Arg Val Ser Pro Pro Leu Thr
 1               5                  10                  15

Thr Gly Pro Pro Glu Phe Glu Arg
            20

<210> 7
<211> 24
<212> PRT
<213> Homo sapiens

<400> 7
Arg Leu Arg Tyr Phe Gln Gly Tyr Ala Arg Ser Ala Gln Leu Arg Leu
 1               5                  10                  15

Ala Pro Leu Tyr Ala Ser Ala Arg
            20

<210> 8
<211> 15
<212> PRT
<213> Homo sapiens

<400> 8
Arg Ala Ala Leu Leu Gly Arg Leu Arg Thr Leu Leu Pro Trp Ala
 1               5                  10                  15

<210> 9
<211> 22
<212> PRT
```

<213> Homo sapiens

<400> 9
Met Lys Asp Glu Val Ala Leu Leu Ala Ala Val Thr Leu Leu Gly Val
 1               5                  10                  15

Leu Leu Gln Ala Tyr Phe
            20